United States Patent
Mitts et al.

(10) Patent No.: US 7,560,430 B2
(45) Date of Patent: Jul. 14, 2009

(54) ELASTIN DIGEST COMPOSITIONS AND METHODS UTILIZING SAME

(75) Inventors: Thomas Mitts, Visalia, CA (US); Felipe Jimenez, San Bernardino, CA (US)

(73) Assignee: Human Matrix Sciences, LLC, Visalia, CA (US)

( * ) Notice: Subject to any disclaimer, the term of this patent is extended or adjusted under 35 U.S.C. 154(b) by 718 days.

(21) Appl. No.: 10/778,253

(22) Filed: Feb. 13, 2004

(65) Prior Publication Data

US 2004/0162232 A1    Aug. 19, 2004

Related U.S. Application Data

(60) Provisional application No. 60/447,461, filed on Feb. 14, 2003.

(51) Int. Cl.
*A61K 38/00* (2006.01)
*C07K 14/00* (2006.01)

(52) U.S. Cl. ......................... 514/12; 530/300
(58) Field of Classification Search ........................ None
See application file for complete search history.

(56) References Cited

U.S. PATENT DOCUMENTS

| | | | |
|---|---|---|---|
| 5,733,572 A * | 3/1998 | Unger et al. ................. | 424/450 |
| 6,232,458 B1 | 5/2001 | Weiss et al. | |
| 6,506,731 B1 | 1/2003 | Sandberg et al. | |
| 6,777,389 B1 * | 8/2004 | Mitts et al. .................... | 514/16 |
| 2003/0166510 A1 | 9/2003 | Pickart | |
| 2005/0059599 A1 * | 3/2005 | Sandberg et al. ............. | 514/12 |
| 2005/0208150 A1 * | 9/2005 | Mitts et al. .................. | 424/639 |
| 2006/0264375 A1 | 11/2006 | Jimenez et al. | |
| 2008/0050346 A1 | 2/2008 | Jimenez et al. | |

OTHER PUBLICATIONS

Tajima et al., "Modulation by elastin peptide VGVAPG of cell proliferation and elastin expression in human skin fibroblasts", Acrh Dermatol Res. 289: 489-492 (1997).*

Mochizuki et al., "Signaling Pathways Transduced through the Elastin Receptor Facilitate Proliferation of Arterial Smooth Muscle Cells", The Journal of Biological Chemistry 277(47): 44854-44863 (2002).*

Martin et al., "Total synthesis and expression in *Escherichia coli* of a gene encoding human tropoelastin", Gene 154: 159-166 (1995).*

Stone et al., "Building Elastin Incorporation of Recombinant Human Tropoelastin into Extracellular Matrices using Nonelastogenic Rat-1 Fibroblasts as a Source for Lysyl Oxidase", Am. J. Respir. Cell Mol. Biol. 24: 733-739 (2001).*

U.S. Appl. No. 11/924,586, Mitts et al., Oct. 25, 2007.

U.S. Appl. No. 11/405,843, Jimenez et al., Apr. 17, 2006.

Hinek et al., Proteolytic digest derived from bovine Ligamentum Nuchase Stimulates deposition of new elastin-enriched matrix in cultures and transplants of human dermal fibroblasts, 2005, J. Dermatol. Sci. 39(3):155-166.

* cited by examiner

*Primary Examiner*—Anand U Desai
(74) *Attorney, Agent, or Firm*—Pepper Hamilton LLP

(57) ABSTRACT

The present invention provides compositions for the therapeutic and/or cosmetic treatment of Elastin comprising tissues. Therapeutic and cosmetic compositions comprising an elastin digest stimulate the endogenous production of Elastin and appear to enhance the elasticity of the skin and provide an external supply of peptide precursors of Elastin that penetrate into the tissue to which it is applied. The present invention describes compositions containing an elastin digest derived from proteolytic digestion of insoluble elastin derived from mammalian ligaments with a protein digesting composition, such as proteinase K. The elastin digest is a mixture of elastin peptides wherein the elastin peptide mixture comprises peptides of the sequence GXXPG, wherein X represents one of the natural amino acids. The elastin digest of the present invention may also comprise epitopes of cytokines, growth factors and di-peptides. Methods of using these elastin digest comprising compositions for treating tissues in need of increased elasticity and or Elastin are described.

33 Claims, 11 Drawing Sheets

(3 of 11 Drawing Sheet(s) Filed in Color)

SEQUENCE LISTING

```
<160> NUMBER OF SEQ ID NOS: 44

<210> SEQ ID NO 1
<211> LENGTH: 5
<212> TYPE: PRT
<213> ORGANISM: BOVINE

<400> SEQUENCE: 1

Gly Ala Ala Pro Gly
1               5

<210> SEQ ID NO 2
<211> LENGTH: 5
<212> TYPE: PRT
<213> ORGANISM: BOVINE

<400> SEQUENCE: 2

Gly Val Val Pro Gly
1               5

<210> SEQ ID NO 3
<211> LENGTH: 5
<212> TYPE: PRT
<213> ORGANISM: BOVINE

<400> SEQUENCE: 3

Gly Gly Gly Pro Gly
1               5

<210> SEQ ID NO 4
<211> LENGTH: 5
<212> TYPE: PRT
<213> ORGANISM: BOVINE

<400> SEQUENCE: 4

Gly Leu Leu Pro Gly
1               5

<210> SEQ ID NO 5
<211> LENGTH: 5
<212> TYPE: PRT
```

```
<213> ORGANISM: BOVINE

<400> SEQUENCE: 5

Gly Ile Ile Pro Gly
1               5

<210> SEQ ID NO 6
<211> LENGTH: 5
<212> TYPE: PRT
<213> ORGANISM: BOVINE

<400> SEQUENCE: 6

Gly Ser Ser Pro Gly
1               5

<210> SEQ ID NO 7
<211> LENGTH: 5
<212> TYPE: PRT
<213> ORGANISM: BOVINE

<400> SEQUENCE: 7

Gly Thr Thr Pro Gly
1               5

<210> SEQ ID NO 8
<211> LENGTH: 5
<212> TYPE: PRT
<213> ORGANISM: BOVINE

<400> SEQUENCE: 8

Gly Cys Cys Pro Gly
1               5

<210> SEQ ID NO 9
<211> LENGTH: 5
<212> TYPE: PRT
<213> ORGANISM: BOVINE

<400> SEQUENCE: 9

Gly Met Met Pro Gly
1               5

<210> SEQ ID NO 10
<211> LENGTH: 5
<212> TYPE: PRT
<213> ORGANISM: BOVINE

<400> SEQUENCE: 10

Gly Phe Phe Pro Gly
1               5

<210> SEQ ID NO 11
<211> LENGTH: 5
<212> TYPE: PRT
<213> ORGANISM: BOVINE

<400> SEQUENCE: 11

Gly Tyr Tyr Pro Gly
1               5

<210> SEQ ID NO 12
<211> LENGTH: 5
<212> TYPE: PRT
<213> ORGANISM: BOVINE
```

```
<400> SEQUENCE: 12

Gly Trp Trp Pro Gly
1               5

<210> SEQ ID NO 13
<211> LENGTH: 5
<212> TYPE: PRT
<213> ORGANISM: BOVINE

<400> SEQUENCE: 13

Gly Asp Asp Pro Gly
1               5

<210> SEQ ID NO 14
<211> LENGTH: 5
<212> TYPE: PRT
<213> ORGANISM: BOVINE

<400> SEQUENCE: 14

Gly Asn Asn Pro Gly
1               5

<210> SEQ ID NO 15
<211> LENGTH: 5
<212> TYPE: PRT
<213> ORGANISM: BOVINE

<400> SEQUENCE: 15

Gly Glu Glu Pro Gly
1               5

<210> SEQ ID NO 16
<211> LENGTH: 5
<212> TYPE: PRT
<213> ORGANISM: BOVINE

<400> SEQUENCE: 16

Gly Gln Gln Pro Gly
1               5

<210> SEQ ID NO 17
<211> LENGTH: 5
<212> TYPE: PRT
<213> ORGANISM: BOVINE

<400> SEQUENCE: 17

Gly Arg Arg Pro Gly
1               5

<210> SEQ ID NO 18
<211> LENGTH: 5
<212> TYPE: PRT
<213> ORGANISM: BOVINE

<400> SEQUENCE: 18

Gly His His Pro Gly
1               5

<210> SEQ ID NO 19
<211> LENGTH: 5
<212> TYPE: PRT
<213> ORGANISM: BOVINE

<400> SEQUENCE: 19
```

```
Gly Lys Lys Pro Gly
1               5

<210> SEQ ID NO 20
<211> LENGTH: 5
<212> TYPE: PRT
<213> ORGANISM: BOVINE

<400> SEQUENCE: 20

Gly Pro Pro Pro Gly
1               5

<210> SEQ ID NO 21
<211> LENGTH: 5
<212> TYPE: PRT
<213> ORGANISM: BOVINE

<400> SEQUENCE: 21

Gly Pro Pro Pro Gly
1               5

<210> SEQ ID NO 22
<211> LENGTH: 5
<212> TYPE: PRT
<213> ORGANISM: BOVINE

<400> SEQUENCE: 22

Gly Pro Pro Pro Gly
1               5

<210> SEQ ID NO 23
<211> LENGTH: 5
<212> TYPE: PRT
<213> ORGANISM: BOVINE

<400> SEQUENCE: 23

Arg Arg Pro Glu Val
1               5

<210> SEQ ID NO 24
<211> LENGTH: 8
<212> TYPE: PRT
<213> ORGANISM: BOVINE

<400> SEQUENCE: 24

Gln Pro Ser Gln Pro Gly Gly Val
1               5

<210> SEQ ID NO 25
<211> LENGTH: 4
<212> TYPE: PRT
<213> ORGANISM: BOVINE

<400> SEQUENCE: 25

Pro Gly Gly Val
1

<210> SEQ ID NO 26
<211> LENGTH: 4
<212> TYPE: PRT
<213> ORGANISM: BOVINE

<400> SEQUENCE: 26

Gly Pro Gly Val
1
```

```
<210> SEQ ID NO 27
<211> LENGTH: 4
<212> TYPE: PRT
<213> ORGANISM: BOVINE

<400> SEQUENCE: 27

Lys Pro Gly Val
1

<210> SEQ ID NO 28
<211> LENGTH: 4
<212> TYPE: PRT
<213> ORGANISM: BOVINE

<400> SEQUENCE: 28

Gly Pro Gly Leu
1

<210> SEQ ID NO 29
<211> LENGTH: 4
<212> TYPE: PRT
<213> ORGANISM: BOVINE

<400> SEQUENCE: 29

Glu Gly Ser Ala
1

<210> SEQ ID NO 30
<211> LENGTH: 4
<212> TYPE: PRT
<213> ORGANISM: BOVINE

<400> SEQUENCE: 30

Pro Gly Gly Phe
1

<210> SEQ ID NO 31
<211> LENGTH: 4
<212> TYPE: PRT
<213> ORGANISM: BOVINE

<400> SEQUENCE: 31

Gly Gly Gly Ala
1

<210> SEQ ID NO 32
<211> LENGTH: 5
<212> TYPE: PRT
<213> ORGANISM: BOVINE

<400> SEQUENCE: 32

Lys Pro Gly Lys Val
1               5

<210> SEQ ID NO 33
<211> LENGTH: 4
<212> TYPE: PRT
<213> ORGANISM: BOVINE

<400> SEQUENCE: 33

Pro Gly Gly Val
1
```

```
<210> SEQ ID NO 34
<211> LENGTH: 4
<212> TYPE: PRT
<213> ORGANISM: BOVINE

<400> SEQUENCE: 34

Lys Pro Lys Ala
1

<210> SEQ ID NO 35
<211> LENGTH: 5
<212> TYPE: PRT
<213> ORGANISM: BOVINE

<400> SEQUENCE: 35

Gly Pro Gly Gly Val
1               5

<210> SEQ ID NO 36
<211> LENGTH: 4
<212> TYPE: PRT
<213> ORGANISM: BOVINE

<400> SEQUENCE: 36

Gly Pro Gln Ala
1

<210> SEQ ID NO 37
<211> LENGTH: 5
<212> TYPE: PRT
<213> ORGANISM: BOVINE

<400> SEQUENCE: 37

Gly Gly Pro Gly Ile
1               5

<210> SEQ ID NO 38
<211> LENGTH: 5
<212> TYPE: PRT
<213> ORGANISM: BOVINE

<400> SEQUENCE: 38

Pro Gly Pro Gly Ala
1               5

<210> SEQ ID NO 39
<211> LENGTH: 5
<212> TYPE: PRT
<213> ORGANISM: BOVINE

<400> SEQUENCE: 39

Gly Pro Gly Gly Val
1               5

<210> SEQ ID NO 40
<211> LENGTH: 4
<212> TYPE: PRT
<213> ORGANISM: BOVINE

<400> SEQUENCE: 40

Gly Gln Pro Phe
1

<210> SEQ ID NO 41
<211> LENGTH: 8
```

```
-continued

<212> TYPE: PRT
<213> ORGANISM: BOVINE

<400> SEQUENCE: 41

Gly Gly Lys Pro Pro Lys Pro Phe
1               5

<210> SEQ ID NO 42
<211> LENGTH: 7
<212> TYPE: PRT
<213> ORGANISM: BOVINE

<400> SEQUENCE: 42

Gly Gly Gln Gln Pro Gly Leu
1               5

<210> SEQ ID NO 43
<211> LENGTH: 4
<212> TYPE: PRT
<213> ORGANISM: BOVINE

<400> SEQUENCE: 43

Met Arg Ser Leu
1

<210> SEQ ID NO 44
<211> LENGTH: 5
<212> TYPE: PRT
<213> ORGANISM: BOVINE

<400> SEQUENCE: 44

Gly Gly Pro Gly Ile
1               5
```

ELASTIN DIGEST COMPOSITIONS AND METHODS UTILIZING SAME

CROSS-REFERENCES

This application claims priority to United States provisional application Ser. No. 60/447,461, filed Feb. 14, 2003 and entitled "Elastin Peptide Fragments and Compositions Comprising Same and Methods of Utilizing Same", herein incorporated by reference in its entirety.

BACKGROUND OF THE INVENTION

Elastin is an amorphous protein present in the elastic fibers of tissues such as arteries, blood vessels, skin, tendons and elastic ligaments, the abdominal wall, and lungs. Unlike other fibrous tissues like collagen, Elastin is unique in that it may be stretched to over 150 percent of its original length but it can rapidly return to its original size and shape. This property of Elastin provides tissues that incorporate it, the required ability to resume their original form after stretching due to blood flow, breathing, or bending. Like collagen protein, Elastin contains about 30% glycine amino acid residues and is rich in proline. Elastin differs from collagen in that it contains very little hydroxyproline and no hydroxylysine. Elastin has a very high content of alanine and also contains two unique amino acids isodesmosine and desmosine. These amino acids are believed to be responsible for Elastin's ability to return to its original shape after stretching.

Tropoelastin is a soluble precursor of Elastin; it is a peptide with a molecular weight in the range of 70-75 kDa. In the arterial tissues tropoelastin is produced and secreted into the extracellular space by smooth muscle cells; in other tissues it is produced in cells, like fibroblast cells, and is also secreted into the extracellular space. In these cells tropoelastin is synthesized by ribosomes in the rough endoplasmatic reticulum and processed by the Golgi apparatus. The soluble tropoelastin molecules secreted (often referred to a Proelastin before secretion) into the extracellular space synthesize to form Elastin filaments and sheets via cross linking of the tropoelastin molecules primarily by crosslinking of lysine amino acid residues to form desmosine and isodesmosine. Mature Elastin is amorphous and contains many cross links which makes it nearly impossible to solubilize.

The resiliency of skin is maintained by elastic fibers in the extracellular matrix (ECM). These ECM components are organized into a networks of rope-like structures and composed of two major components: an amorphous core, consisting of extensively crosslinked elastin which makes up the bulk (>90%) of the fiber; and the 10-12-nm microfibrils made up of several distinct glycoproteins.

In various tissue or biological functions, inelastic collagen fibers may be interwoven with the Elastin to limit stretching of the Elastin and prevent tearing of Elastin comprising tissue. Elastic fibers may also contain glycoproteins as microfibrils, which may serve to organize tropoelastin molecules secreted into the extracellular space for later crosslinking. Examples of such glycoproteins include laminin, which is large glycoprotein and a major component of basement membranes and is made by all epithelial cells, and fibronectin which is a cell-surface and blood glycoprotein involved in a variety of cell surface phenomena.

Combinations of components of the extracellular matrix have been incorporated into cosmetic compositions. Elastin is insoluble due to its high degree of cross linking at its lysine residues and also because of its high content (about 75%) of hydrophobic amino acids (Gly, Val, Ala, Pro). In some instances, normally cross-linked insoluble Elastin (i.e., insoluble in water, organic solvents, and physiological fluids such as saline and blood) is rendered soluble using a variety of chemical and enzymatic methods to cleave insoluble Elastin protein and form smaller peptide fragments.

The human skin consists of two layers; a superficial layer called the epidermis which is epithelial tissue and a deeper layer called the dermis that is primarily connective tissue. These two layers are bound together to form skin which varies in thickness from less than about 0.5 mm, to 3 or even 4 millimeters. The connective tissue found in skin is essentially an intricate meshwork of interacting, extracellular molecules that constitute the so-called "extracellular matrix". The extracellular matrix includes proteins that are secreted locally and are widely distributed in the extracellular matrix. The main types of proteins that make up the matrix include collagens, Elastin, fibronectin and laminin. Normal elastic fiber assembly is visualized as a spider web spanning the dermis. Exposure of the skin to ultraviolet and visible light from the sun, wind, and chemicals leads to loss of moisture in the epidermal layers and degradation of the Elastins present in the skin. Loss of elasticity in skin primarily occurs because of an overproduction of poorly assembled elastic fibers induced by exposure to sunlight. These poorly assembled elastic fibers can be visualized as "clumps" in the dermoepidermal junction and papillary dermis and is commonly referred to as solar elastosis. These effects, result in loss of skin elasticity, tone and texture, are collectively referred to as aging of the skin. Loss of elasticity in elastic tissues such as arteries is mainly due to calcification and glycation of elastic fibers.

Until recently, elastin, the major component of elastic fibers, was thought to have primarily a mechanical role in providing tissue resiliency. This view was challenged by results of in vitro studies indicating that soluble fragments of tropoelastin and elastin degradation products may bind to the cell surface Elastin Binding Protein (EBP) and stimulate proliferation and migration of human skin fibroblasts, lymphoblasts, smooth muscle cells and cancer cells.

SUMMARY OF THE INVENTION

The present invention provides compositions for the therapeutic and/or cosmetic treatment of Elastin comprising tissues. Preferably such compositions stimulate the endogenous production of Elastin or appear to enhance the elasticity of the skin and provide an external supply of peptide precursors of Elastin that penetrate into the tissue to which it is applied.

The present invention describes compositions containing an elastin digest derived from proteolytic digestion of insoluble elastin derived from mammalian ligaments with a protein digesting composition. The elastin digest is a mixture of elastin peptides wherein the elastin peptide mixture comprises peptides of the sequence GXXPG, wherein X represents one of the natural amino acids (i.e., SEQ ID NO: 45). The elastin digest of the present invention may also comprise epitopes of cytokines, growth factors and di-peptides. Composition embodiments of the present invention may further comprise excipients and other additives. The protein digesting composition may be human elastase enzyme or proteinase K enzyme.

Embodiments of the present invention are compositions for therapeutic and/or cosmetic treatment of Elastin comprising tissues. Such compositions may improve the Elastin content, elasticity, functionality and appearance of the tissue to which it is applied. The compositions preferably provide an elastin digest which may penetrate, permeate or diffuse the tissue to which such compositions are administered. Such compositions may improve the endogenous production of Elastin in these tissues.

Another embodiment of the present invention describes a process of deriving an elastin digest comprising purifying insoluble elastin from mammalian ligaments and digesting the insoluble elastin with a protein digesting composition.

Another embodiment of the present invention relates to a therapeutic skin care product comprising an elastin digest. Another embodiment of the present invention relates to a method for clinically treating a patient's facial lines and wrinkles comprising administering a composition comprising an elastin peptide mixture to sites presenting visible lines and wrinkles.

In another embodiment of the invention, a method of treating a tissue comprising administering to a site in need thereof on a mammal an effective amount of a therapeutic composition comprising an elastin digest. The method may be used to treat tissue in need of Elastin due to loss of existing Elastin in the tissue, loss of elastic properties of existing Elastin, or need to increase endogenous Elastin production. The composition comprising the elastin digest is administered in an amount sufficient to improve the elastic properties of the tissue and may further comprise an elastin tissue compatible excipient. Administering of the elastin digest composition establishes an effective concentration of the composition at the site in need and may include use of the digest dissolved or dispersed in various excipients including but not limited to aqueous solutions, creams, tablets, intravenous solutions, or aerosols. Administering of the composition is performed as needed to maintain an effective therapeutic concentration of the peptide digest comprising composition at the tissue site for ameliorating the condition of the tissue.

Another embodiment of the present invention is a method of treating an Elastin comprising tissue, the method comprising administering to a site in need thereof on a mammal an effective amount of a composition comprising an elastin digest, for improving the elasticity or appearance of said tissue.

Another embodiment of the present invention relates to a method of stimulating the production of fibrillin and cell proliferation in fibroblasts. Another embodiment of the present invention relates to a method of stimulating the deposition and synthesis of elastin in fibroblasts. Another embodiment of the present invention relates to a method of stimulating the deposition of collagen and lysyl oxidase in fibroblasts. Another embodiment of the invention relates to a method of stimulating cell migration to age-depleted zones of the skin. Another method of the invention relates to a method of inhibiting the production of chrondroctin sulfate-containing glycosaminoglycans.

The compositions and methods in the embodiments of the present invention are advantageous in that elastin digest compositions may be useful for therapeutic and or cosmetic treatment of Elastin comprising tissues. It is further advantageous that such compositions and methods may be used to stimulate the endogenous production of Elastin and provide an external supply of precursors of Elastin that penetrate into the tissues to which it is applied. Such peptide compositions may induce migration of nascent (due to increased cell proliferation induced by Elastin receptor binding peptide) dermal fibroblasts to "age-depleted" zones in skin such as the dermoepidermal junction and papillary dermis which lack cellularity as one ages.

In part, other aspects, features, benefits and advantages of the embodiments of the present invention will be apparent with regard to the following description and appended claims.

DESCRIPTION OF THE DRAWINGS

The file of this patent contains at least one drawing executed in color. Copies of this patent with color drawing(s) will be provided by the Patent and Trademark Office upon request and payment of necessary fee.

DETAILED DESCRIPTION OF THE INVENTION

Figure 1:
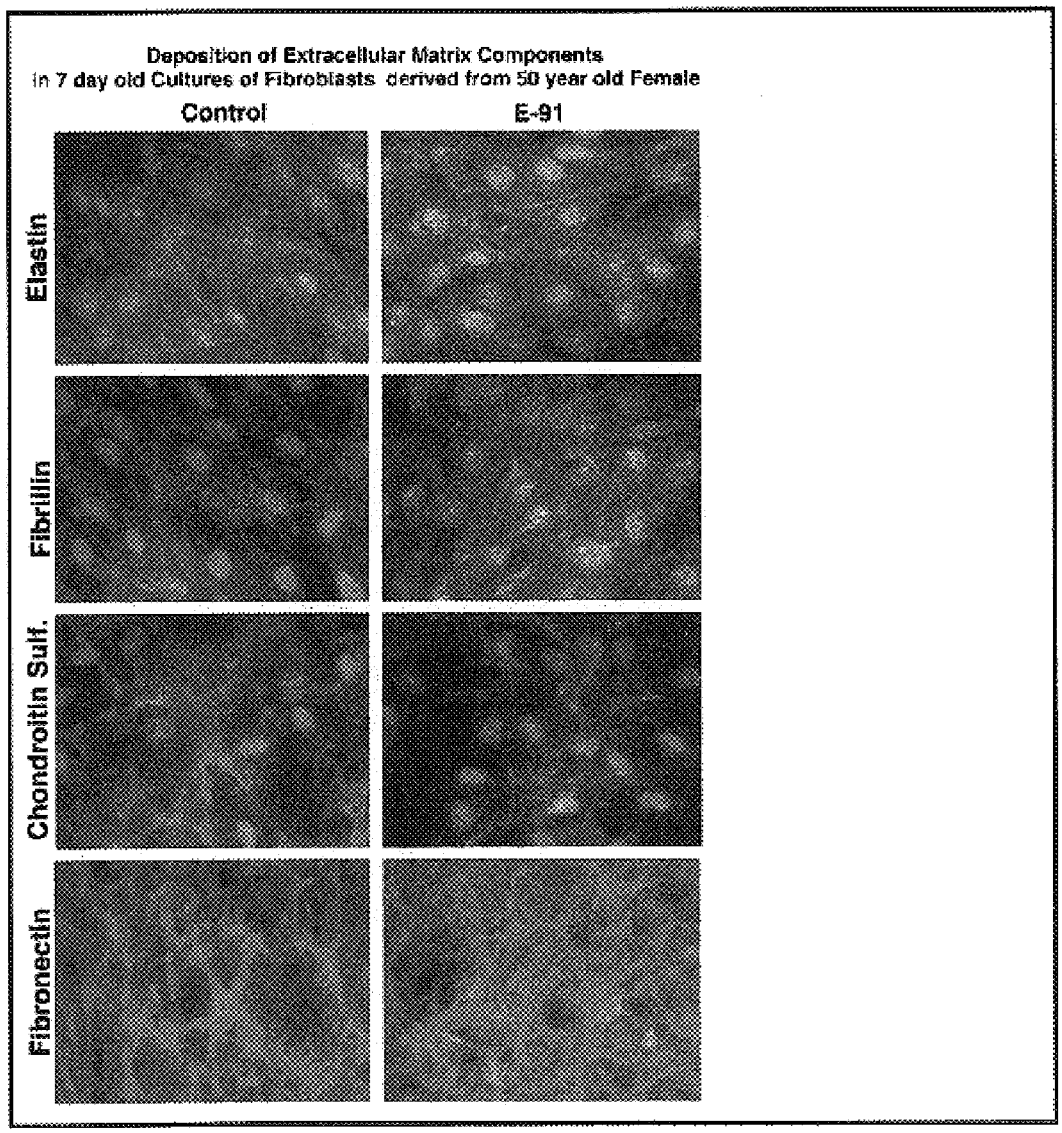
FIG. 1 is an assessment of the deposition of insoluble elastin in fibroblasts.

Before the present composition and methods are described, it is to be understood that this invention is not limited to the particular molecules, compositions, methodologies or protocols described, as these may vary. It is also to be understood that the terminology used in the description is for the purpose of describing the particular versions or embodiments only, and is not intended to limit the scope of the present invention which will be limited only by the appended claims.

It must also be noted that as used herein and in the appended claims, the singular forms "a", "an", and "the" include plural reference unless the context clearly dictates otherwise. Thus, for example, reference to a "cell" is a reference to one or more cells and equivalents thereof known to those skilled in the art, and so forth. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference. Nothing herein is to be construed as an admission that the invention is not entitled to antedate such disclosure by virtue of prior invention.

The methods herein for use contemplate prophylactic use as well as curative use in therapy of an existing condition. As used herein, the term "about" means plus or minus 10% of the numerical value of the number with which it is being used. Therefore, about 50% means in the range of 45%-55%. In order that the invention herein described may be more fully understood, the following detailed description is set forth.

The term as used herein, "elastin digest", refers to any insoluble Elastin derived from mammalian tissue or previously solubilized Elastin (either chemically or enzymatically) that is proteolytically digested with a protein digesting composition.

Embodiments of the present invention relate to compositions comprising an elastin digest which improves the appearance, the elasticity, and/or the Elastin content of mammalian tissue. The compositions containing the elastin digest of the present invention may induce the synthesis of fibrillin and collagen in cell cultures. Additionally, the compositions may induce elastogenesis in cells derived from subjects of different ages.

Suitable elastin digests may be obtained from proteolytic digestion, with a protein digesting composition, of insoluble Elastin derived from connective mammalian tissues or ligaments, bovine neck ligaments in particular. Suitable protein digesting compositions, include for example, human elastase enzyme, Proteinase K enzyme, and thermolysin.

Suitable digests may be derived from connective tissue, such as mammalian ligaments. Generally, the ligament is manually freed of excess connective tissue, fat and muscle then pulverized. The mulch is boiled in water to remove soluble proteins then boiled in alkali to remove resistant protein. The washed insoluble mulch is hydrolyzed then again boiled in water, purified on cellulose and lyophilized. The resulting peptide digest is highly soluble in water, buffers and detergents. The molecular weight range by gel filtration chromatography of about 1,000 to 60,000 Da of this digest indicate the presence of a mixture of polypeptides. These polypeptides contain the cross-linking amino acids desmosine and isodesmosine. The digest may also comprises other extracellular matrix components and di-peptides. The resulting peptide digest contains peptides having an amino acid consisting of the sequence GXXPG (where X may be any of the 20 natural amino acids) (i.e., SEQ ID NO: 45). The sequence GXXPG contains motifs such as VGVAPG (i.e., SEQ ID NO: 46), PGGVLPG (i.e., SEQ ID NO: 47), VGVVPG (i.e., SEQ ID NO: 48), and IGLGPGGV (i.e., SEQ ID NO: 49). It is known that peptides having the GXXPG motif stimulate cell migration and proliferation. Extracellular matrix components include Fibrillin I, a major component of microfibrillin scaffold of elastic fibers, collagen type I, II and III, fibronectin chondroiton sulfate-containing glycosaminoglycans, elastin, and lysyl oxidase. Composition embodiments of the present invention may stimulate the synthesis of one or more of the extracellular matrix components within fibroblasts.

Generally speaking, the term "tissue" refers to any aggregation of similarly specialized cells which are united in the performance of a particular function. As used herein, "tissue", unless otherwise indicated, refers to tissue which includes Elastin as part of its necessary structure and/or function. For example, connective tissue which is made up of, among other things, collagen fibrils and Elastin fibrils satisfies the definition of "tissue" as used herein. Additionally, Elastin appears to be involved in the proper function of blood vessels, muscles, veins, and arteries in their inherent elasticity. Unless otherwise indicated, the term "skin" means that outer integument or covering of the body, consisting of the dermis and the epidermis and resting upon subcutaneous tissue.

As used herein, the term "therapeutic" means an agent utilized to treat, combat, ameliorate, prevent or improve an unwanted condition or disease of a patient. In part, embodiments of the present invention are directed to improve the functionality, the appearance, the elasticity, and/or the Elastin content of mammalian tissue. As it applies to skin, it is measured by elasticity, turgor, tone, appearance, degree of wrinkles, and youthfulness. As the term applies to blood vessels it may be measured by the degree of elasticity or proper vasomotor response (vasodilatation/vasoconstriction) of the vessel. Accordingly, therapeutic treatment of blood vessels may have implications in diseases associated with elasticity, including hypertension, arteriosclerosis, angina, angiogenesis, myocardial infarction, coronary thrombosis, restenosis post angioplasty, and chronic obstructive pulmonary disease.

The term "cosmetic," as used herein, refers to a beautifying substance or preparation which preserves, restores, bestows, stimulates, or enhances the appearance of bodily beauty or appears to enhance the beauty of youthfulness, specifically as it relates to the appearance of tissue or skin. The term "modify" is used to convey that the present invention changes either the appearance, form, characteristics and/or the physical attributes of the tissue to which it is being provided, applied or administered. The change in form may be demonstrated by any of the following alone or in combination: enhanced appearance of the skin; increased softness of the skin; increased turgor of the skin; increased texture of the skin; increased elasticity of the skin; decreased wrinkle formation and increased endogenous Elastin production in the skin, increased firmness and resiliency of the skin.

Embodiment compositions of the present invention comprise an elastin digest. For example, commercially available, Elastin E91 preparation from Protein Preparations, Inc., St. Louis, Mo., is a suitable elastin product to subject to digestion, having about 1,000 to 60,000 dalton molecular weight. Additionally, a series of digests available under the trade name ProK, and specifically ProK60, are Elastin peptide mixture derived from the proteolytic digestion of insoluble Elastin derived from bovine neck ligaments, commercially available from Human Matrix Sciences, LLC. The digestion is accomplished with Proteinase K enzyme. the commercially available products will be referred to as E91 and ProK respectively.

Elastin does not contain the RGD sequence and does not interact with cell surface integrins. Previous studies demonstrated that numerous cell types, including fibroblasts express the cell surface elastin receptor complex which consists of three subunits and that the average cell contains approximately $2 \times 10^6$ elastin binding sites. Two of those subunits (55-kDa and 61-kDa) are anchored to the plasma membrane, while the third, a peripheral 67-kDa protein, actually binds elastin. This major functional component of the receptor complex was named the elastin binding protein (EBP). The repeat hexapeptide in tropoelastin, VGVAPG (i.e., SEQ ID NO: 46), has been identified as a chief ligand for high affinity binding to this cell surface receptor. It has been later established that diverse peptides maintaining a GXXPG sequence (wherein X is any of the 20 nature amino acids) (i.e., SEQ ID NO: 45), including the LGTIPG sequence (i.e., SEQ ID NO: 50) present on the domain V of B1 chain of laminin, can also bind to the EBP and induce similar cellular effects.

It has been established that interaction between the peptides of the elastin digest and EBP residing on surface of several cell types results in a rapid and transient increase in free intracellular $Ca^{++}$, and that the EBP-mediated opening of calcium channels involves pertussis toxin-sensitive G proteins and activation of phospholipase C and protein kinase C in fibroblasts and lymphocytes. Other studies revealed that the EBP-dependent chemotactic response of macrophages to elastin-derived peptides also involves stimulation of cGMP and cGMP-dependent protein kinase. Recently it was found that elastin receptor-transduced signaling triggers activation of G proteins, opening of L-type calcium channels and a sequential activation of tyrosine kinases; FAK, c-Src, PDGF-receptor kinase and then Ras-Raf-MEK1/2-ERK1/2 phosphorylation cascade. This, in turn, causes an increase in expression of cyclins and cyclin-dependent kinases, and a consequent increase in cellular proliferation. It was also found that the EBP transduces signals leading to tyrosine kinase-dependent phosphorylation of β-tubulin α-actin and troponin-T, that could be linked to reorganization of cytoskeleton and increased cellular motility. The data also indicate that treatment with elastin-based peptides lead to secretion and activation of elastinolytic and collagenolytic matrix metallo-proteinases (MMPs) and secretion of new extracellular matrix. The presence of the peptides represented in SEQ ID NO: 23-44 as seen in Table 1, confirm that elastin digests of the present invention interact with cell surface receptors as described above.

Stimulation of elastin receptors concurrently activates signaling pathways for cellular proliferation and reorganization of cytoskeleton. This has been described in an article by Hinek, J. Biol. Chem., 2002 Nov. 22; 277(47): 44854-63, herein incorporated by reference. This stimulation has also been linked to cell migration. Migration of nascent dermal fibroblasts to age-depleted zones in skin such as the dermopedermal junction and papillary dermis is thus possible to stimulate. Age-depleted zones of the skin are areas that lack cellularity.

Since cutaneous aging associates with a marked decrease in number of fibroblasts and gradual thinning and disappearances of elastic fibers in entire dermis, one embodiment of the present invention is the selection of the most active preparation of an elastin digest that would rejuvenate human skin, by stimulation of fibroblasts proliferation and migration, as well as induction of their ability to synthesize a new elastin-enriched matrix.

In one embodiment of the present invention, compositions improve facial lines and wrinkles through induction of new connective tissues synthesis in skin. The compositions are used for the restoration of cutaneous connective tissue proteins in the skin. The present invention relates to cosmetic skin care products based on biologically active elastin digest. An elastin digest may be formulated into a cosmetic skin care product to aid or facilitate the assembly of new elastic fibers in skin. An elastin digest may also be formulated into fibroblast injections for the clinical treatment for the improvement of facial lines and wrinkles through cell culture of patient dermal fibroblasts and re-introduction via injection into sites presenting visible lines and wrinkles.

Compositions of the present invention preferably comprise a mixture of peptides made with elastin and/or collagen comprising tissue, or previously digested proteins, that have been digested with a digesting protein composition. Preferably, the digesting protein composition is enzyme proteinase K or human elastase enzyme. The compositions may be cosmetic, pharmacological, or therapeutic and are useful for treating mammalian tissue. It has been found that the elastin digest of the present invention comprises at least one peptide SEQ ID NO: 23-44. Please refer to Table 1. More specifically, about 25% of the total peptide sequence of an insoluble elastin proteolytically digested with human elastase enzyme is represented by the amino acid sequences found in SEQ ID NO: 23-44. Any one of the twenty standard amino acid may be present in the elastin peptide digest composition as well as 3-hydroxyproline and 4-hydroxyproline. Additionally, the elastin digest of the present invention comprises other epitopes for extracellular matrix proteins, cytokines, and growth factors, di-peptides. An elastin digest typically comprises peptides which have molecular weights ranging from about 200 Da to about 18,000 Da.

Compositions of the present invention may also further comprise such peptides fused or chemically bonded to a substrate in order to produce beneficial elastic biomaterials such as elastic cartilage by the method and materials disclosed in U.S. Pat. No. 6,372,228, the contents of which are incorporated herein by reference in their entirety. Di-peptides of Elastin digested with proteinase K may also be present in the compositions of the present invention, examples of such di-peptides are listed in Table 2.

Additives which aid in improving the elasticity of elastin comprising tissues such as Tretinoin, vitamin E, sources of copper, zinc, and/or magnesium ions, Retinol, copper peptides, and any one of the 20 standard amino acids may also be added to the compositions of the present invention. Additives which induce deposition of tropoelastin on microfibril scaffolds, and compounds which induce lysyl oxidase activity, such as transforming growth factor beta1, may also be added to such compositions. Compositions of the present invention may include a therapeutically and biologically compatible excipient.

In another embodiment of the invention, compositions comprise other additives, such as hyaluronic acid. In another embodiment of the present invention, a method of clinical treatment for the improvement of facial lines and wrinkles through injection of a hyaluronic acid/biologically active elastin digest into sites presenting visible lines and wrinkles is provided. In such injections, the hyaluronic acid will act as a resorbable scaffold for dermal fibroblasts infiltration. The biologically active elastin digest serves to induce fibroblast proliferation and migration into the hyaluronic acid scaffold.

An elastin digest may comprise a mixture of elastin peptides and other components, including other epitopes for extracellular matrix proteins, cytokines and growth factors. The presence of other epitopes, cytokines and growth factors have been observed in several elastin digests. These additional components of an elastin peptide digest may include tropoelastin, the peptide VGVAPG (i.e., SEQ ID NO: 46), desmosine, tropo-Exon 36, fibrillin, 1, MAGP 1, LTBP2, versican, collagen type I, collagen type IV, fibronectin, EBP, PDGF, bFGF, FGF, and IL-1B.

Fibrous protein tissue comprising Elastin or collagen-like tertiary structures and tropoelastin are examples of proteins and peptides which may be digested to produce elastin digests of the present invention. Protein, peptides, Elastin or tropoelastin may be obtained from various animal tissues. Other protein sources may be any suitable for cleavage by hydrolytic or enzymatic reaction to yield peptides SEQ ID NO: 23-44. Any connective tissue comprising Elastin is suitable as a source to form an elastin digest of the present invention. A source of protein for the Elastin is animal tissue. The elastic ligaments prominent in the necks of grazing animals, such as cows, horses, pigs and sheep, are especially rich in Elastin; preferably the protein source is insoluble bovine Elastin. Aorta is also rich in Elastin. Elastin may be obtained from these tissues by mild hydrolysis of neck tendons and aorta respectively of young animals, which have first been cleaned, defatted and pulverized. Elastin suitable for use in the present invention can be prepared by the methods and materials, for example, from bovine nuchal ligament, fibrinogen and thrombin as described and incorporated herein by reference in U.S. Pat. No. 5,223,420. Elastin may also be obtained from digestion of Elastin comprising tissues including arteries (e.g. coronary or femoral arteries, for example, from swine), umbilical cords, intestines, ureters, skin, lungs, etc. from such grazing animals. Any method of removing cellular material, proteins and fats from the native matrix while leaving the extracellular Elastin matrix intact can be used. These methods can involve a combination of acidic, basic, saline, detergent, enzymatic, thermal or erosive means, as well as the use of organic solvents such as chloroform and methanol. This may include—incubation in solutions of sodium hydroxide, formic-acid, trypsin, guanidine, ethanol, diethylether, —acetone, t-butanol, and sonication.

Elastin may be digested using a variety of chemicals as well as enzymes. The optimal temperature and time (of incubation depend on the starting material and digestive agent used and can be readily determined based upon the resulting digestion peptide products. Typically, the digestion of Elastin comprising tissue to produce peptides proceeds more quickly at higher temperatures. For example Elastin may be treated with potassium hydroxide ethanol mixtures or with boiling oxalic acid to chemically digest Elastin to yield peptides of the Elastin. Various enzymes, such as thermolysin and elastase (enzyme in stomach of mammals for digesting meats) as well as collagenase, trypsin, and chymotrypsin may be used to prepare peptides of Elastin and are available from Elastin Products Co., St. Louis, Mo. Thermolysin is a preferred digestion composition and is generally described as a proteolytic enzymatic obtained from the bacterium *Bacillus thermoproteolyticus*, which hydrolyses the N-terminal amide bonds of hydrophobic amino acid residues in proteins. Digestion with thermolysin or other suitable digestion compositions may occur at temperatures around about 55° C.

In a preferred embodiment, an elastin digest containing peptides SEQ ID NO: 23-44 for the compositions of the present invention may be prepared by digestion of Elastin comprising tissue with a digestion composition comprising proteinase K available from Sigma Co., St. Louis, Mo. The digestion composition may contain proteinase K, proteinase K in a suitable solvent, or proteinase K with other enzymes and or acids, bases, or buffers. Proteinase K will proteolytically digest most fibrous proteins including keratin and collagen. The mixture of peptides from the digestion may be those with an amino acid sequence known to bind to the Elastin receptor of cells, SEQ ID NO: 1-22 which are capable of binding to the Elastin receptor of cells. Please refer to Table 1 for SEQ ID NO: 1-44. Proteinase K may be used to digest partially digested Elastin prepared by other chemical or enzymatic treatments. Lysis products from proteinase K digestion of Elastin comprising tissue may be mixed with the lysis products from digestion of Elastin comprising tissue with other chemicals or enzymes in the compositions of this invention.

An elastin digest may be purified by methods including but not limited to affinity chromatography, molecular sieve chromatography, dialysis, ultrafiltration, and combinations of these. Analysis of peptides from the digestion reactions or of purified peptides may be performed using Edman degradation sequencing, LC/MS/MS, electrophoresis, MALDI-TOF, circular dichroism, NMR and other methods known to those skilled in the art.

One embodiment of the present invention is directed to compositions comprising elastin digests which contain peptides that are homologous with portions of elastin found in the tissue of the mammal to be treated with such compositions. Such homologous elastin digests may be useful as a therapeutic and/or cosmetic composition or agent for modifying tissue, especially skin. Such homologous elastin digests may be obtained by enzymatic cleavage of Elastin comprising tissue such as bovine ligamentum nuchae with a composition comprising proteinase K.

In one embodiment of the present invention, a composition comprising an elastin digest is used as a cosmetic. One or more peptides of the elastin digest may penetrate, diffuse, or permeate into the tissue to which it is applied; preferably one or more peptides of the elastin digest have a molecular weight of about 10,000 to 30,000 Daltons.

The concentration of the elastin peptide composition in the composition is in a range from about 0.0002% to about 90% by weight with the balance of the composition comprised of an excipients and/or supplements such as vitamin E.

As used herein, the terms "pharmaceutically acceptable", "physiologically tolerable", and grammatical variations thereof, as they refer to compositions, carriers, diluents and reagents, are used interchangeably and represent that the materials are capable of administering upon a mammal without the production of undesirable physiological effects such as nausea, dizziness, rash, or gastric upset. In a preferred embodiment, the therapeutic composition is not immunogenic when administered to a human patient for therapeutic purposes.

The preparation of a pharmacological composition that contains active ingredients dispersed therein is well understood in the art. Typically such compositions if desired, may be prepared as sterile compositions either as liquid solutions or suspensions, aqueous or non-aqueous, however, suspensions in liquid prior to use can also be prepared.

An elastin digest may be mixed with excipients which are pharmaceutically acceptable and compatible with the active ingredient and in amounts suitable for use in the therapeutic methods described herein. Various excipients may be used as carriers for the peptide digest compositions of the present invention as would be known to those skilled in the art. For example, a peptide digest may be dissolved in excipients such as water comprising solutions, alcohol comprising mixture, intravenous and saline comprising mixture, dextrose, glycerol, ethanol or the like and combinations thereof. In addition, if desired, the composition can contain minor amount of auxiliary substances such as wetting or emulsifying agents, pH buffering agents and the like which enhance the effectiveness of the active ingredient. Formulations comprising a elastin digest, for example those prepared by the proteolytic digestion of insoluble elastin with at least one peptide of SEQ ID NO: 23-44, may be prepared by mixing such excipients with the soluble elastin digest. The digest in the formulation comprises from about 0.0002 to about 90% by weight of the formulation. These formulations may be employed directly as a constituent of therapeutic or cosmetic treatments, such as emulsions, lotions, sprays, ointments, creams and foam masks. Final products may contain up to 10% by weight but preferably 0.001 to 5% of such a solution though of course more concentrated or more dilute solutions may also be used in greater or lesser amounts. For example, an eye cream may comprise about 0.1% (w/w) and a facial cream may comprise about 0.025% (w/w) of a soluble elastin digest in an excipient. Facial cream composition usually comprise salts. Specifically, the elastin digest of the present invention exists in cosmetic or therapeutic compositions at concentrations of about 10-1000 µg/ml, preferably about 25 µg/ml.

A therapeutic composition of the present invention can include pharmaceutically acceptable salts of the components therein. Pharmaceutically acceptable salts include the acid addition salts (formed with the free amino groups of the peptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers and excipients are well known in the art. Other equivalent terms include physiologically acceptable or tissue compatible. Exemplary of liquid carriers are sterile aqueous solutions that contain no materials in addition to the active ingredients and water, or contain a buffer such as sodium phosphate at physiological pH value, physiological saline or both, such as phosphate-buffered saline and Tris-HCl buffer. Still further, aqueous carriers can contain more than one buffer salt, as well as salts such as sodium and potassium chlorides, dextrose, propylene glycol, polyethylene glycol and other solutes.

Compositions comprising an elastin digest may be formulated into gels, creams and lotions. Liquid compositions can also contain liquid phases in addition to and to the exclusion of water. Exemplary of such additional liquid phases and glycerin, vegetable oils such as cottonseed oil, organic esters such as ethyl oleate, and water-oil emulsions. In such compositions the peptides of the peptide digest are wet by the liquid or they may be soluble in the liquid. An elastin digest may be mixed with gels, creams, or ointments and may include but are not limited to petroleum jelly and coco butter. In these mixtures the peptide digest may be in the form of a suspension or form a gel with the excipient. The digest may be mixed with solids such as starches and methyl cellulose.

Additionally, in other embodiment of the invention, compositions comprising an elastin digest may contain chemical preservatives, such as cetylpyridinium chloride, K-Sorbate, Na-Benzoate, various parabens, and/or other chemical preservatives. Other suitable additives in the therapeutic compositions of the present invention include sodium compounds and copper based compounds. Compounds comprising sodium are suitable additives for therapeutic compositions of the present invention. Sodium has been linked to stimulate elastogenesis. Compounds comprising copper are another suitable additives in the therapeutic compositions of the present invention.

A therapeutically effective amount of a composition comprising an elastin digest is a predetermined amount calculated to achieve the desired effect, i.e., to effectively promote improved tissue elasticity or the appearance of skin. In addition, an effective amount can be measured by improvements in one or more symptoms occurring in a mammal. A therapeutically effective amount of peptide digest of this invention is typically an amount such that when it is administered in a physiologically tolerable excipient composition, it is sufficient to achieve an effective local concentration in the tissue. Effective amounts of compounds of the present invention can be measured by improvements in tissue elasticity, endogenous Elastin production, tissue function (elasticity), or tissue appearance and tone.

The terms "therapeutically effective" or "effective", as used herein, may be used interchangeably and refer to an amount of a therapeutic composition of the present invention—e.g., one comprising an elastin digest. For example, a therapeutically effective amount of a composition comprising an elastin peptide digest is a predetermined amount calculated to achieve the desired effect, i.e., to effectively promote Elastin production, cell proliferation, or improved appearance, or improved tissue elasticity in an individual to whom the composition is administered. An elastin digest would appear to have far-ranging therapeutic effect, including cardiovascular disease and in wound healing.

Thus, the dosage ranges for the administering of a digest of the invention are those large enough to produce the desired effect in which the condition to be treated is ameliorated. The dosage should not be so large as to cause adverse side effects. Generally, the dosage will vary with the age, condition, and sex of the patient, and the extent of the disease in the patient, and can be determined by one of skill in the art. The dosage can be adjusted in the event of any complication. The term "unit dose" when used in reference to a therapeutic composition of the present invention refers to physically discrete units suitable as unitary dosage for the subject, each unit containing a predetermined quantity of active material, i.e., an elastin digest, calculated to produce the desired therapeutic effect in association with the required diluent; i.e., excipient, carrier, or vehicle.

The compositions are administered in a manner compatible with the dosage formulation, and in a therapeutically effective amount. A therapeutic amount of an elastin digest composition of this invention is an amount sufficient to produce the desired result, and can vary widely depending upon the disease condition and the potency of the therapeutic compound. In the present invention the desired result is an improvement in elasticity of the tissue as determined by an improvement in the Elastin content of the tissue, improved capacity and function of the tissue, or improved appearance, suppleness, and/or tone of the tissue being treated. The quantity to be administered depends on the subject to be treated, the capacity of the subject's system to utilize the active ingredient, and the degree of therapeutic effect desired. Precise amounts of active ingredient required to be administered depend on the judgment of the practitioner and are peculiar to each individual. However, suitable dosage ranges for systemic application are disclosed herein and depend on the conditions of administering. Suitable regimes for administration are also variable, but are typified by an initial administration followed by repeated doses at one or more time intervals by a subsequent administration. Where a single composition is not available for a treatment, or where such a composition is not desirable, administration of composition may also comprise the application of several different compositions sequentially to achieve a desired therapeutic effect.

"Providing" when used in conjunction with a therapeutic means to administer a therapeutic directly into or onto a target tissue or to administer a therapeutic to a patient whereby the therapeutic positively impacts the tissue to which it is targeted. Thus, as used herein, the term "providing", when used in conjunction with elastin digest, can include, but is not limited to, providing an elastin digest into or onto the target tissue; providing an elastin digest systemically to a patient by, e.g., intravenous injection whereby the therapeutic reaches the target tissue; providing an elastin digest in the form of the encoding sequence thereof to the target tissue (e.g., by so-called gene-therapy techniques). "Providing" a composition may be accomplished by injection, topical administration, or by either method in combination with other known techniques. Such combination techniques include heating, radiation and ultrasound.

Heating of a site on a patient comprising tissue is known to open pores, activate the various mechanisms of a cell, and increase diffusion into said tissue and cells. Heating in connection with providing a therapeutic composition to a site comprising connective tissue is therefore a preferred embodiment of the present invention.

Embodiments of the present invention may involve local administration of a pharmacologically active peptide comprising composition to a tissue site on a mammal, and therefore is best expressed in unit dosage form. Such local administration is typically by topical or local administration of a liquid or gel composition. Thus a therapeutic composition can be administered via a solid, semi-solid (gel) or liquid composition, each providing particular advantages for the route of administration.

An elastin digest may be administered parenterally by injection or by gradual infusion over time. For example, elastin digest may be administered topically, locally, perilesionally, perineuronally, intracranially, intravenously, intrathecally, intramuscularly, subcutaneously, intracavity, transdermally, dermally, or via an implanted device, and they may also be delivered by peristaltic means. Although local topical delivery is desirable, there are other means of delivery, for example: oral, parenteral, aerosol, intramuscular, subcutaneous, transcutaneous, intramedullary, intrathecal, intraventricular, intravenous, intraperitoneal, or intranasal administration. The diffusion of the one or more peptides of the digest composition into the tissue may be facilitated by application of external heat or soaking of skin in a heated solution comprising an effective amount of the composition.

Alternatively, continuous administration, i.e. intravenous infusion or topical application, sufficient to maintain therapeutically effective concentrations in the tissue are contemplated. Therapeutically effective tissue concentrations of an elastin digest are in the range of about 0.00002 to 90% (w/w). Preferably, the elastin digest exists in compositions at concentrations of about 10-1000 µg/ml, preferably 25 µg/ml.

Regardless of the method of administration of the composition, one or more peptides of the composition penetrate the tissue to which it is applied. Penetration for purposes of this invention is used equivalently with diffusion or permeation of the one or more components of the composition into the tissue to effect a desired therapeutic effect.

An elastin digest may be administered as a pharmaceutical composition in the form of a solution, gel or suspension. However, therapeutic compositions of the present invention may also be formulated for therapeutic administration as a tablet, pill, capsule, aerosol, liposomes, sustained release formulation, or powder.

It is further contemplated that an elastin digest may be used therapeutically in a variety of applications. For example, as described above, a variety of useful compositions and formats, including bioabsorbable material or matrices may be used in conjunction with the peptides of the present invention to treat tissues requiring Elastin.

Suitable applications of the present invention include therapeutic compositions comprising an elastin digest for use in oral applications, such as compositions to be applied to gums and other connective tissue and ligaments in the mouth. For example, compositions comprising an elastin digest may be incorporated into toothpastes or mouthwashes in order to provide a therapeutic composition for rebuilding connective tissue in the mouth. Additionally, other periodontal and orthodontic applications are possible, such as providing a therapeutic composition comprising an elastin digest to the gums of patients who wear braces or other orthodontic devices in order to heal minor ulcerations that result on the gums or mouth tissue from the devices.

Another embodiment of the present invention is therapeutic composition comprising an elastin digest to be used to strengthen elastic fibers around follicles, in order to prevent hair loss. Strengthening follicles containing hair by the use of a therapeutic composition is within the scope of the present invention. A therapeutic composition may be provided to the site on a patient that contains follicles. Elastin production around the follicle will strengthen said follicle and thus prevent hair loss at the site.

A further application according to another embodiment of the present invention is a therapeutic composition comprising an elastin digest to treat ophthalmologic injuries or conditions, such as a corneal ulceration. A therapeutic composition may be provided to a site which comprises connective tissue. A therapeutic composition may be provided to a site which exhibits a ophthalmologic injury or condition in order to stimulate the production of elastin and collagen and/or to induce cellular proliferation of said connective tissue.

Various tissues in a mammal may suffer from a condition or state where loss of Elastin has occurred, where the existing Elastin present in the tissue has lost its elasticity, or where the endogenous production of Elastin or tropoelastin in the tissue is inadequate. Such tissue is in need of Elastin as may be identified by a loss of tissue elasticity, reduced capacity or loss of required tissue elastic function, loss of appearance or suppleness, or loss of tone. Once identified, such tissue may be treated with the compositions of this invention. A composition comprising an elastin digest promotes cellular proliferation in wrinkle sites lacking cellularity.

In another embodiment of the invention, a method of inhibiting the production of chondroitin sulfate-containing glycosaminoglycans is provided. Inhibiting such production may be helpful for example in sun-damaged skin. Such inhibition of chondroitin sulfate expression aids in the deposition of newly synthesized elastin and helps to decrease solar elastosis.

The elastin digests which have been identified as being useful in the present invention comprise at least one amino acid sequence listed in Table 1. Preferably about 25% of the elastin digest's sequences is represented by the sequences listed in Table 1.

TABLE 1

| SEQ ID NO:. | Peptide | Position Cleavage Site | Mol. Wt | Name |
| --- | --- | --- | --- | --- |
| SEQ ID NO:1 | GAAPG | | | Glycine-Alanine-Alanine-Proline-Glycine |
| SEQ ID NO:2 | GVVPG | | | Glycine-Valine-Valine-Proline-Glycine |
| SEQ ID NO:3 | GGGPG | | | Glycine-Glycine-Glycine-Proline-Glycine |
| SEQ ID NO:4 | GLLPG | | | Glycine-Leucine-Leucine-Proline-Glycine |
| SEQ ID NO:5 | GIIPG | | | Glycine-Isoleucine-Isoleucine-Proline-Glycine |
| SEQ ID NO:6 | GSSPG | | | Glycine-Serine-Serine-Proline-Glycine |
| SEQ ID NO:7 | GTTPG | | | Glycine-Threonine-Threonine-Glycine |
| SEQ ID NO:8 | GCCPG | | | Glycine-Cysteine-Cysteine-Proline-Glycine |
| SEQ ID NO:9 | GMMPG | | | Glycine-Methionine-Methionine-Proline-Glycine |
| SEQ ID NO:10 | GFFPG | | | Glycine-Phenylalanine-Phenylalanine-Proline-Glycine |
| SEQ ID NO:11 | GYYPG | | | Glycine-Tyrosine-Tyrosine-Proline-Glycine |
| SEQ ID NO:12 | GWWPG | | | Glycine-Tryptophan-Tryptophan-Proline-Glycine |
| SEQ ID NO:13 | GDDPG | | | Glycine-Aspartic Acid-Aspartic Acid-Proline-Glycine |
| SEQ ID NO:14 | GNNPG | | | Glycine-Asparagine-Asparagine-Proline-Glycine |
| SEQ ID NO:15 | GEEPG | | | Glycine-Glutamic Acid-Glutamic Acid-Proline-Glycine |
| SEQ ID NO:16 | GQQPG | | | Glycine-Glutamine-Glutamine-Proline-Glycine |
| SEQ ID NO:17 | GRRPG | | | Glycine-Arginine-Arginine-Proline-Glycine |

TABLE 1-continued

| SEQ ID NO: | Peptide | Position Cleavage Site | Mol. Wt | Name |
|---|---|---|---|---|
| SEQ ID NO:18 | GHHPG | | | Glycine-Histidine-Histidine-Proline-Glycine |
| SEQ ID NO:19 | GKKPG | | | Glycine-Lysine-Lysine-Proline-Glycine |
| SEQ ID NO:20 | GPPPG | | | Glycine-Proline-Proline-Proline-Glycine |
| SEQ ID NO:21 | G3Hyp3HypPG | | | Glycine-3-hydroxyproline-3-hydroxyproline-Proline-Glycine |
| SEQ ID NO:22 | G4Hyp4HypPG | | | Glycine-4-hydroxyproline-4-hydroxyproline-Proline-Glycine |
| SEQ ID NO:23 | RRPEV | 13 | 655.377 | Arginine-Arginine-Proline-Glutamic Acid-Valine |
| SEQ ID NO:24 | QPSQPGGV | 29 | 768.377 | Glutamine-Proline-Serine-Glutamine-Proline-Glycine-Glycine-Valine |
| SEQ ID NO:25 | PGGV | 37 | 328.175 | Proline-Glycine-Glycine-Valine |
| SEQ ID NO:26 | GPGV | 60 | 328.175 | Glycine-Proline-Glycine-Valine |
| SEQ ID NO:27 | KPGV | 67 | 399.248 | Lysine-Proline-Glycine-Valine |
| SEQ ID NO:28 | GPGL | 75 | 342.190 | Glycine-Proline-Glycine-Leucine |
| SEQ ID NO:29 | EGSA | 81 | 362.144 | Glutamic Acid-Glycine-Serine-Alanine |
| SEQ ID NO:30 | PGGF | 90 | 376.175 | Proline-Glycine-Glycine-Phenylalanine |
| SEQ ID NO:31 | GGGA | 97 | 260.112 | Glycine-Glycine-Glycine-Alanine |
| SEQ ID NO:32 | KPGKV | 150 | 527.343 | Lysine-Proline-Glycine-Lysine-Valine |
| SEQ ID NO:33 | PGGV | 163 | 328.175 | Proline-Glycine-Glycine-Valine |
| SEQ ID NO:34 | KPKA | 190 | 442.29 | Lysine-Proline-Lysine-Alanine |
| SEQ ID NO:35 | GPGGV | 246 | 385.196 | Glycine-Proline-Glycine-Glycine-Valine |
| SEQ ID NO:36 | GPQA | 265 | 371.180 | Glycine-Proline-Glutamine-Alanine |
| SEQ ID NO:37 | GGPGI | 294 | 399.212 | Glycine-Glycine-Proline-Glycine-Isoleucine |
| SEQ ID NO:38 | PGPGA | 597 | 397.196 | Proline-Glycine-Proline-Glycine-Alanine |
| SEQ ID NO:39 | GPGGV | 615 | 385.196 | Glycine-Proline-Glycine-Glycine-Valine |
| SEQ ID NO:40 | GQPF | 704 | 447.212 | Glycine-Glutamine-Proline-Phenylalanine |
| SEQ ID NO:41 | GGKPPKPF | 723 | 826.470 | Glycine-Glycine-Lysine-Proline-Proline-Lysine-Proline-Phenylalanine |
| SEQ ID NO:42 | GGQQPGL | 213 | 655.329 | Glycine-Glycine-Glutamine-Glutamine-Proline-Glycine-Leucine |
| SEQ ID NO:43 | MRSL | 4 | 505.268 | Methionine-Arginine-Serine-Leucine |
| SEQ ID NO:44 | GGPGI | 294 | 399.212 | Glycine-Glycine-Proline-Gycline-Isoleucine |

Refer to Table 1. A UV chromatogram of Elastin E91 and the location of experimentally determined peptide sequences on bovine tropoelastin sequence was conducted. Elastin E91 is a suitable elastin digest of the present invention. The GXXPG sequence (i.e., SEQ ID NO: 45) accounts for about 25% of the total peptide sequence constituting the elastin digest. Without wishing to be bound by theory, it seems the peptides containing the sequences PGGVLPG (i.e., SEQ ID NO: 47), VGVVPG (i.e., SEQ ID NO: 48), and IGLGPGGV (i.e., SEQ ID NO: 49) are effective in permeating the stratum corneum of the skin. Table 1 offers a list of sequences that constitute about 25% of an elastin digest.

Immuno-characterization of E91 and various Pro K formulation reveal the presence of epitopes for extracellular matrix proteins, cytokines and growth factors. These formulations also comprise peptides listed in Table 1. ProK formulations contain various peptides, of which about 25% are represented by the sequences in Table 1. Elastin digests described herein may also comprise di-peptides. Suitable di-peptides found in the digests are listed in Table 2.

TABLE 2

| Position of Cleavage Site | Di-peptide | Molecular Weight | Name |
|---|---|---|---|
| 20 | CI | 234.104 | Cysteine-Isoleucine |
| 48 | GL | 188.116 | Glycine-Leucine |
| 77 | GA | 146.069 | Glycine-Alanine |
| 106 | KA | 217.143 | Lysine-Alanine |
| 130 | ST | 206.090 | Serine-Threonine |
| 171 | RF | 321.180 | Arginine-Phenylalanine |
| 182 | PT | 216.111 | Proline-Threonine |
| 192 | QV | 245.138 | Glutamine-Valine |
| 200 | GI | 188.116 | Glycine-Isoleucine |
| 215 | PL | 228.147 | Proline-Leucine |
| 217 | GY | 238.095 | Glycine-Tyrosine |
| 219 | PI | 228.147 | Proline-Isoleucine |
| 221 | KA | 217.143 | Lysine-Alanine |
| 226 | PA | 186.095 | Proline-Alanine |
| 232 | PY | 278.127 | Proline-Tyrosine |

TABLE 2-continued

| Position of Cleavage Site | Di-peptide | Molecular Weight | Name |
|---|---|---|---|
| 234 | KT | 247.153 | Lysine-Tyrosine |
| 241 | GF | 222.1 | Glycine-Phenylalanine |
| 257 | PT | 216.11 | Proline-Threonine |
| 276 | KL | 259.190 | Lysine-Leucine |
| 344 | GV | 174.100 | Glycine-Valine |
| 449 | KI | 259.190 | Lysine-Isoleucine |
| 497 | QF | 293.138 | Glutamine-Phenylalanine |
| 557 | RA | 245.149 | Arginine-Alanine |
| 738 | CL | 234.104 | Cysteine-Leucine |

Accordingly, therapeutic and cosmetic compositions comprising elastin digests comprise amino acids of the formula Gly-Xaa-Xbb-Pro-Gly, where in Xaa and Xbb are any one of the 20 standard amino acids, 3-hydroxyproline, and 4-hydroxyproline, or therapeutically acceptable acid addition salts thereof (i.e., SEQ ID NO: 51). In these peptides, the amino acids Xaa and Xbb may be the same or different amino acids. Such compositions may be prepared by reaction of Elastin comprising tissue with a digesting composition comprising proteinase K. The amino acids Listed in SEQ ID NO: 23-44 represent about 25% of the amino acids identified in an elastin digest.

The various embodiments of the present invention may be used to improve the elasticity, cell proliferation, endogenous Elastin production, function, and/or appearance of properties of tissues by providing a source of extracellular Elastin homologous segments in the form of an elastin digest. Such Elastin segments may cross link within the extracellular peptides, may contain sequences known to bind the Elastin receptor, and may provide additional benefits such as Elastin stimulation of Elastin production. The invention may be applied to tissue in a therapeutically effective amount for the treatment of various diseases.

An advantage of this invention is that an elastin digest provides a source of soluble Elastin containing peptide segments and/or Elastin receptor binding peptides. Such a composition containing an elastin digest may stimulate native tropoelastin production within the cell, may result in cell proliferation, and may also provide a secondary source of peptide segments from Elastin for cross linking in the extracellular matrix of cells to which it is applied.

The compositions of the present invention containing an elastin digest derived from the proteolytic digestion of insoluble elastin derived from mammalian ligaments with a protein digesting composition have been shown to have the following in vitro effects. The compositions upregulate fibrillin 1, type 1 and lysyl oxidase. The compositions induce synthesis and deposition of elastin and induce collagen cellular proliferation in normal human dermal fibroblasts across various ages. The following effects in fibroblast culture compositions are better understood in reference to the examples below.

Examples of compositions and method of making compositions of the present invention are shown by the non-limiting examples below.

EXAMPLE 1

An elastin digest may be any elastin peptide mixture derived from mammalian tissue. For example, the following steps may be used to prepare an elastin digest. Specifically, ProK formulations manufactured by Human Matrix Sciences, is an elastin peptide mixture that may be prepared as follows. Bovine neck ligaments are obtained from local meat packer and obtain USDA certification on the geographic origin of donor cattle. All or most of fat and extraneous connective tissue is removed from dissected bovine neck ligaments. The neck ligaments are ground into small pieces by first running through coarse grind then fine grind modes on an industrial meat grinder. The ground neck ligaments are then suspended in aqueous 1% NaCl at a ratio of 100 gm tissue to 3 liter 1% NaCl. The mixture is stirred for 24 hours at 4° C. to extract soluble connective tissue proteins from ground neck ligaments. The extract from ground ligaments is removed by pouring mixture through a fine mesh kitchen strainer. The ground ligaments are washed twice with 1% NaCl and twice with double-distilled water. The ground ligaments are transferred to erlenmyer flasks and resuspended in double-distilled water. The mixture is autoclaved at 30 PSI for 6 hours to solublilize collagen and other remaining connective tissue proteins. The solubilized connective tissue proteins is removed from insoluble elastin by pouring mixture through a Whatman paper filter. The insoluble elastin is washed twice with boiling double-distilled water and twice with double-distilled water at room temperature. The insoluble elastin is transferred onto glass beaker and extract lipids with a 2:1 ratio of chloroform/methanol (v/v) for 24 hours. Enough chloroform/methanol is added to completely cover insoluble elastin and manually stir mixture until insoluble elastin is evenly resuspended. The chloroform/methanol is removed from defatted insoluble elastin by running mixture through a sintered glass filter under vacuum. The defatted insoluble elastin is dried under a vacuum hood for 8 hours and then over $P_2O_5$ for an additional 16 hours or until constant weight is achieved. The purified insoluble elastin is milled to 50 micron particle size using a Wiley Mill. The milled insoluble elastin is stored in a dessicator at room temperature.

In an alternative method, Elastin E60 (Elastin Products, Co., St. Louis, Mo.) may be used in the compositions and methods of the present invention. E60, Elastin, Particle Size: 100-400 Mesh (149-37 Micron) may be used as an elastin digest provided that the purification methodology is similar to that listed above.

After preparing the milled insoluble elastin in the above steps, it must be digested with Proteinase K or other suitable protein digestion compositions. The purified and milled insoluble Elastin is resuspended in double-distilled water at a ratio of 5 gm Elastin to 1 liter of water (v/v). The mixtures are equilibrated to 40, 45, 50, 55 or 60° C. respectively in order to produce 5 preparations of digested elastin. Please refer to the elastin preparation key below for nomenclature of each of the 5 elastin digest preparations:

| Name | Digestion Temp (° C.) |
| --- | --- |
| ProK 40 | 40 |
| ProK 45 | 45 |
| ProK 50 | 50 |
| ProK 55 | 55 |
| ProK 60 | 60 |

All of the above elastin digest preparations are produced in the same manner except for digestion temperature. Next, the mixture is adjusted to pH 7.5-8.5 with 0.1N NaOH. Then, Ca2+ (Calcium Acetate) is added to obtain a final concentration of 2 mM. The Proteinase K is added to mixture at a ratio of 10 mg enzyme to 1 gm Elastin. Specific activity for Proteinase K should be =30 units/mg protein. The pH of the digest is continuously titrated with 0.1N NaOH to maintain a pH of 7.5-8.5. The digest is allowed to proceed for 75 minutes with constant mixing or agitation.

In an alternative method, the purified and milled insoluble elastin is resuspended in 50 mM Tris-HCl buffer (pH 8.5) at a ratio of 5 gm Elastin to 1 liter of buffer (w/v). The mixture is then equilibrated to 50° C. Calcium Acetate is added to obtain a final concentration of 2 mM. Proteinase K is added to mixture at a ratio of 10 mg enzyme to 1 gm Elastin. Specific activity for Proteinase K should be equal to 30 units/mg protein. The digest is allowed to proceed for 4 hours with constant mixing or agitation.

Once digestion is complete, the elastin digest must be filtered. The digest is run through a 10,000 Da cutoff tangential flow filter made from regenerated cellulose. Filtration of the digest will remove Proteinase K and the digest may contain 10,000 Da Elastin polypeptides. Next, the elastin peptides must be lyophilized and sterilized. The resulting elastin peptides are lyophilized to a dry powder and sterilized via gamma irradiation or micro filtration.

EXAMPLE 2

The following example details a formulation of a composition of the present invention and a method for making such a composition using an already hydrolyzed form of elastin, such as Elastin E91 or ProK. In Phase A, where the ingredient (% w/w) is purified water the quantity is QSAD 100.00. Where the ingredient is Glycerin 99.50%, the range is 5.0 to 15.0 (% w/w), preferably 10.0 (% w/w). Where the ingredient is Methyparaben, the range is 0.004 to 0.40 (% w/w) from Ueno, preferably 0.20 (% w/w). Where the ingredient is Ethylparaben, the range is 0.002 to 0.20 (% w/w) from Ueno, preferably 0.10 (% w/w). In Phase C, where the ingredient is Butylparaben, the range is 0.002 to 0.20 (% w/w) from Ueno, preferably 0.10 (% w/w). Where the ingredient is Propylparaben, the range is 0.001 to 0.20 (% w/w) from Ueno, preferably 0.10 (% w/w). Where the ingredient is Squalane, the range is 0.05 to 10.00 (% w/w) from Robeco, preferably 5.00 (% w/w). Where the ingredient is Caprylic/Capric Triglyceride, the range is 0.04 to 10.00 (% w/w) from Lipo, preferably 5.00 (% w/w). Where the ingredient is Finsolv TN, the range is 0.05 to 10.00 (% w/w) from Finetex, preferably 5.00 (% w/w). In Phase E, where the ingredient is purified water the quantity is 1.00. In Phase F, where the ingredient is Phenoxyethanol, the range is 0.001 to 2.00 (% w/w) from Nipa, preferably 1.00 (% w/w). Where the ingredient is Evening Primrose Oil, the range is 0.001 to 0.20 (% w/w) from Barnet, preferably 0.10 (% w/w). Where the ingredient is Borage Oil, the range is 0.001 to 0.20 (% w/w) from Barnet, preferably 0.10 (% w/w). Where the ingredient is Tocopherol, the range is 0.001 to 0.20 (% w/w) from Roche, preferably 0.10 (% w/w).

The composition may be made by adding Phase A to a first vessel and heating to about 180° F. (about 82° C.). To this vessel is added Phase B by slowly sprinkling it into this vessel with strong agitation until the Carbopol is completely hydrated. Phase C ingredients are added into a second vessel and heated with mixing at about 180° F. (about 82° C.) until the mixture is uniform at which point it is added to the mixture with agitation in the first vessel. The pH of the mixture in the first vessel is adjusted by adding Phase D to the vessel until the mixture has a pH in the range of about 5.5 to about 6.0. This pH adjusted mixture is cooled with gentle mixing to about 100° F. (about 38° C.). In another vessel Phase E ingredients are mixed until the Elastin E91 is completely dissolved; this mixture is added to the first vessel at about 100° F. (about 38° C.) and mixed completely. Phase F ingredients are added to the main vessel at a temperature of about 100° F. (about 38° C.) with mixing, the mixture is cooled.

EXAMPLE 3

The following is a prophetic example illustrating the preparation and administration of a therapeutic composition according to one embodiment of the present invention. Insoluble Elastin from bovine neck ligament is prepared and digested with proteinase K using the materials and methods described in Example 1. A sample of the filtrate from the digestion of the insoluble bovine Elastin with proteinase K was analyzed via LC/MS/MS and the resultant chromatograph peaks identifying the peptides. A possible cleavage of ELS_BOVIN (P04985) from SWISS-PROT and cleaved with Proteinase K using the PeptideCutter program from the ExPASy web site on the world wide web URL address us.expasy.org, gives the peptides and cleavages sites corresponding to SEQ ID NO: 23-44 in Table 1 and di-peptides listed in Table 2.

The remaining filtrate was purified by affinity chromatography with a receptor protein bound to the chromatographic support to isolate the peptide of interest (e.g. SEQ ID NO: 44). The purified peptide was removed from the chromatographic support and was lyophilized to a dry powder and sterilized with gamma radiation or microfiltration. This powder was mixed with 90 grams of purified water, 10 grams of glycerin, 99.5%, and 0.1 grams of lyophilized peptide to make a composition for inducing Elastin excretion.

Therapeutic treatment of a mammalian skin tissue in need of Elastin may occur with treating the skin with a composition from the Examples or any example that will stimulate Elastin synthesis. Next, the skin was treated with the composition prepared and comprising an elastin digest to induce Elastin production. The effectiveness of the treatment, including concentration of the compositions was measured by the improved appearance elasticity of the tissue.

EXAMPLE 4

The following is a prophetic example illustrating the preparation and administration of a therapeutic composition comprising an elastin digest formed in Example 1. About 0.025%-0.1% of the digest was formulated in a composition for treating the skin. This composition is applied to the skin twice daily or as directed. The effectiveness of the treatment, including concentration of the compositions and application schedule, was measured by the improved elasticity and appearance of the tissue.

EXAMPLE 5

Please refer to Table 1 which illustrates the composition of E91. A chromatogram of E91 and sequencing of bovine tropoelastin amino acids were conducted. E91 is derived from bovine tropoelastin and thus contains similar sequencing. An immunocharacterization of E91 and an immunostaining of E91 reveal that E91 contains several extracellular matrix components, including epitopes for extracellular matrix proteins, cytokines and growth factors.

The Peptide Sequence of Elastin E-91 was determined. LC-MS-MS analysis illustrates the presence of five GXXPG containing peptides (i.e., SEQ ID NO: 45). These peptides, listed in Table 1, represent about 25% of the total sequence of the elastin digest. The peptides of E-91 such as PGGVLPG (i.e., SEQ ID NO: 47), VGVVPG (i.e., SEQ ID NO: 48), and IGLGPGGV (i.e., SEQ ID NO: 49) permeate the stratum corneum of the skin due to their small molecular weights. E91 is not a pure mixture of elastin peptides but also contains epitopes for other extracellular matrix proteins and growth factors. E91 may contain di-peptides listed in Table 2. Immunoblotting procedure indicated that E91, in addition to elastin, contain numerous epitopes of other matrix components and several growth factors.

EXAMPLE 6

The biological effects of Elastin E91 were tested in cultures of skin fibroblasts derived from healthy Caucasian females of different ages: 50 years old, 26 years old and 3 years old. Refer to FIGS. 1-4. All of these fibroblasts were originally isolated by digestion of skin biopsies with mixture of 0.25% collagenase type I (Sigma) and 0.05% DNAse type 1 (Sigma) and then passaged by trypsinization and maintained in alpha-minimum essential medium supplemented with 20 mM Hepes, 1% antibiotics/antimycotics, 1% L-Glutamate and 5% fetal bovine serum (FBS). In all experiments the consecutive passages 3-7 were tested. In some experiments the serum free medium was also used.

All above mentioned fibroblasts derived from the skin of normal females were cultured in the presence or absence of various concentrations (in the range 10-100 µg/ml) of E91. Deposition of extracellular matrix components; including elastin, fibrillin I, collagen type I, was assessed in 5-10 days old cultures by immunohistochemistry with the panel of specific antibodies.

Production of the insoluble elastin, the major component of elastic fibers was assessed biochemically after metabolic labeling of cultured fibroblasts with [$^3$H]-valine. Cellular proliferation rates of fibroblasts cultures in the presence and absence of all tested compounds was assessed by incorporation of [$^3$H]-thymidine, by assay of total DNA and immunochemical detection of proliferative antigen ki 67.

Refer to FIG. 1 which illustrates the deposition of extracellular matrix in the fibroblasts. Morphometric analysis of cultures immunstained with antibodies recognizing components of extracellular matrix demonstrated that E91 significantly stimulated production of fibrillin 1, a major components of microfibrillar scaffold of elastic fibers, in cell line derived from the 50 year old patients. The E91 significantly inhibited production of chondroitin sulfate-containing glycosaminoglycans in cultures of fibroblasts derived from subjects of different ages. Inhibition of chondroitin sulfate expression in sun damaged skin may aid in deposition of newly synthesized elastin and help to decrease solar elastosis.

Figure 2:
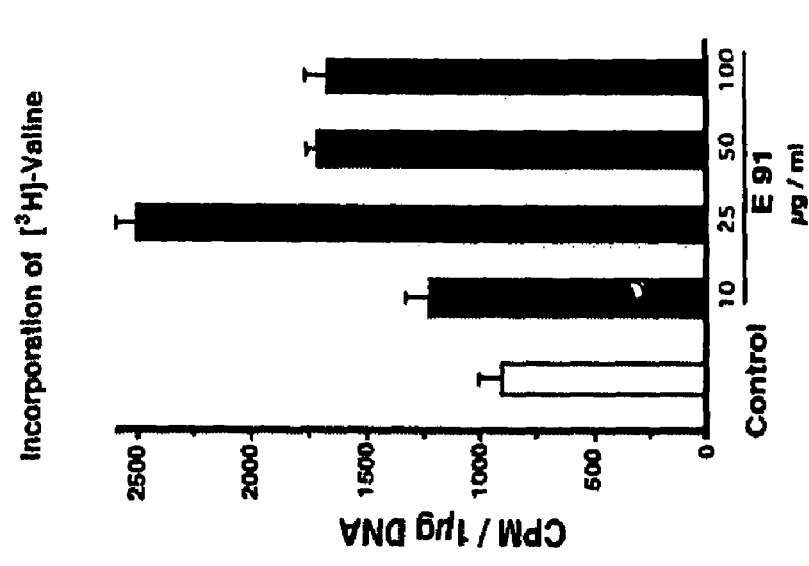
FIG. 2 is an assessment of the deposition of insoluble elastin in fibroblasts.
Figure 3:
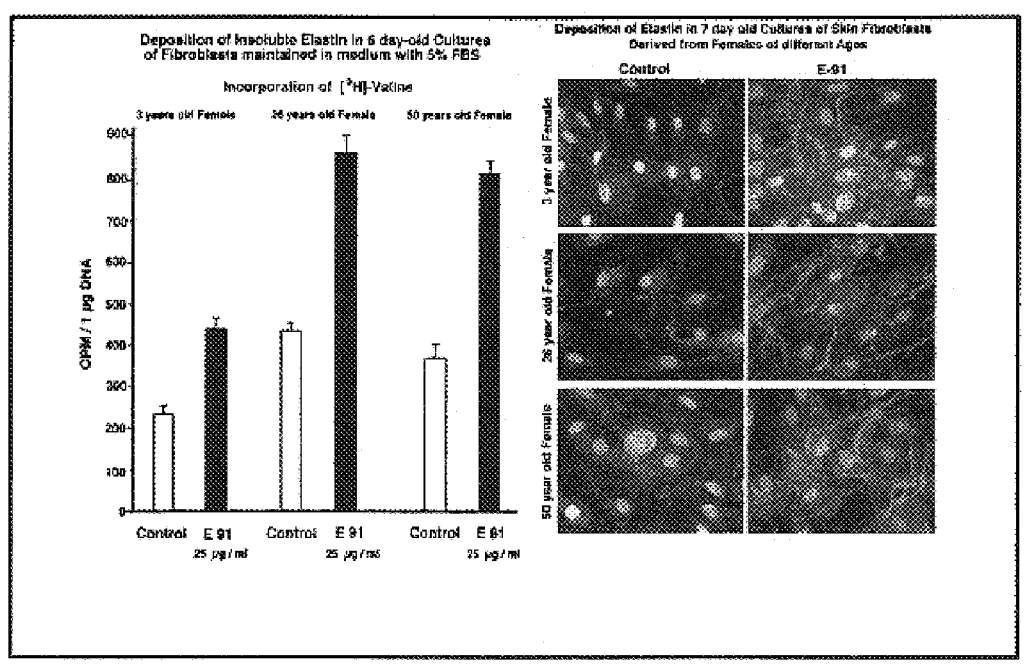
FIG. 3 is an assessment by the incorporation of $[^3H]$-thymidine of the cell proliferation of fibroblasts.

Biochemical assay of newly produced insoluble elastin (metabolically) labeled with radioactive valine) further indicates that E91 stimulates deposition of cross-linked insoluble elastin. Refer to FIG. 2, which illustrates a biochemical assay that shows that deposition of insoluble elastin in fibroblasts from the 50 year old patient. FIG. 3 illustrates the deposition of insoluble elastin in skin fibroblasts derived from different aged subjects. The significant stimulation of elastogenesis was visible at a concentration of 10 µg/ml, and most effective at a concentration of 25 µg/ml. See FIG. 3. The elastogenic effect of E91 was very similar and reproducible in cultures of fibroblasts from all tested subjects (across various ages) and confirmed by immunostaining with specific anti-elastin antibody. See FIGS. 2-3.

Figure 4:
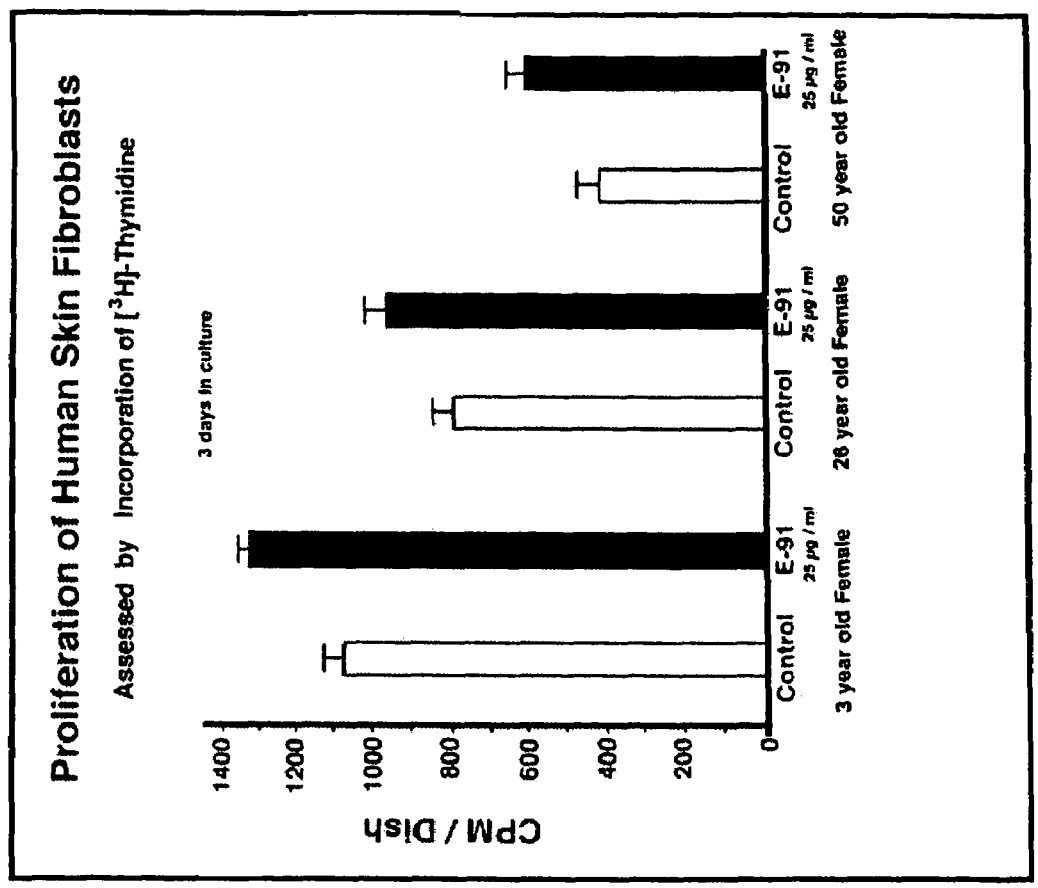
FIG. 4 is assessment of the proliferation of fibroblasts induced with E91.

FIG. 4 illustrates the proliferation of human skin fibroblasts from various aged subjects. Cell proliferation assessed by incorporated of [$^3$H]-thymidine to fibroblasts derived from all three female subjects of different ages has indicated that E91 (25 µg/ml) preparation has a mild mitogenic activity and stimulated cellular proliferation of treated fibroblast by an average of 15-22% over the control. The proliferation effect of E91 was also confirmed by an assay of total DNA assay and by immunochemical detection or proliferation antigen Ki67 (data not shown).

EXAMPLE 7

ProK is an Elastin peptide mixture produced via proteolytic (with proteinase K enzyme) digestion of insoluble bovine Elastin derived from the neck ligaments. ProK is a mixture of peptides having the GXXPG (where X may be any of the 20 natural amino acids; i.e., SEQ ID NO: 45) motif such as VGVAPG (i.e., SEQ ID NO: 46). It is known that peptides having the GXXPG motif stimulate cell migration and proliferation via the 67 Kda Elastin binding protein in several cell lines including dermal fibroblasts and induce gene expression of pro-MMP-1 [1-7].

Results of LC/MS/MS analysis confirm the presence of GXXPG-containing peptides (i.e., SEQ ID NO: 45) in all five ProK preparations. See Table 1. Interestingly, there are differences in peptide sequences between each of the ProK preparations between ProK 40, ProK 50, and ProK 60. These differences in resulting peptide sequences may be due to the non-specific nature of the Proteinase K enzyme with regard to cleavage specificity. In addition, it is also likely that increased temperature induced denaturing in the structure of elastin molecules thus further exposing potential cleavage sites to the Proteinase K enzyme. However, all ProK for mulations are suitable Elastin based compounds of the present invention.

EXAMPLE 8

ProK peptide digests contain a number of components immunoblotting procedure has indicated that all tested preparations contain numerous epitopes of other matrix components, cytokines and several growth factors.

Biological activities of the ProK preparations, differing in the temperature at which bovine insoluble elastin was proteolytically digested with Proteinase K enzyme, were determined as seen in FIGS. 5-11. The biological effects of ProK 40, ProK 50 and ProK 60 were tested in cultures of skin fibroblasts derived from healthy Caucasian females of different ages. 50 years old, 26 years old and 3 years old. The fibroblasts were originally isolated by digestion of skin biopsies with mixture of 0.25% collagenase type I (Sigma) and 0.05% DNAse type 1 (Sigma) and then passaged by trypsinization and maintained in alpha-minimum essential medium supplemented with 20 mM Hepes, 1% antibiotics/antimycotics, 1% L-Glutamine and 5% fetal bovine serum (FBS). In all experiments the consecutive passages 3-7 were tested. In some experiments the serum free medium was also used.

All above mentioned fibroblasts derived from the skin of normal females were cultured in the presence or absences of different concentrations (10-100 µg/ml) of ProK 40, ProK 50 and ProK 60. Deposition of extracellular matrix components, including elastin, fibrillin 1, and collagen type I was assessed in 5-10 days old cultures by immunohistochemistry with the panel of specific antibodies.

Production of the insoluble elastin, the major component of elastin fibers was assessed biochemically after metabolic labeling of cultural fibroblasts with [$^3$H]-valine. Induction of cellular proliferation was assessed by assay of total DNA and immunochemical detection of proliferative antigen ki 67.

Figure 5:
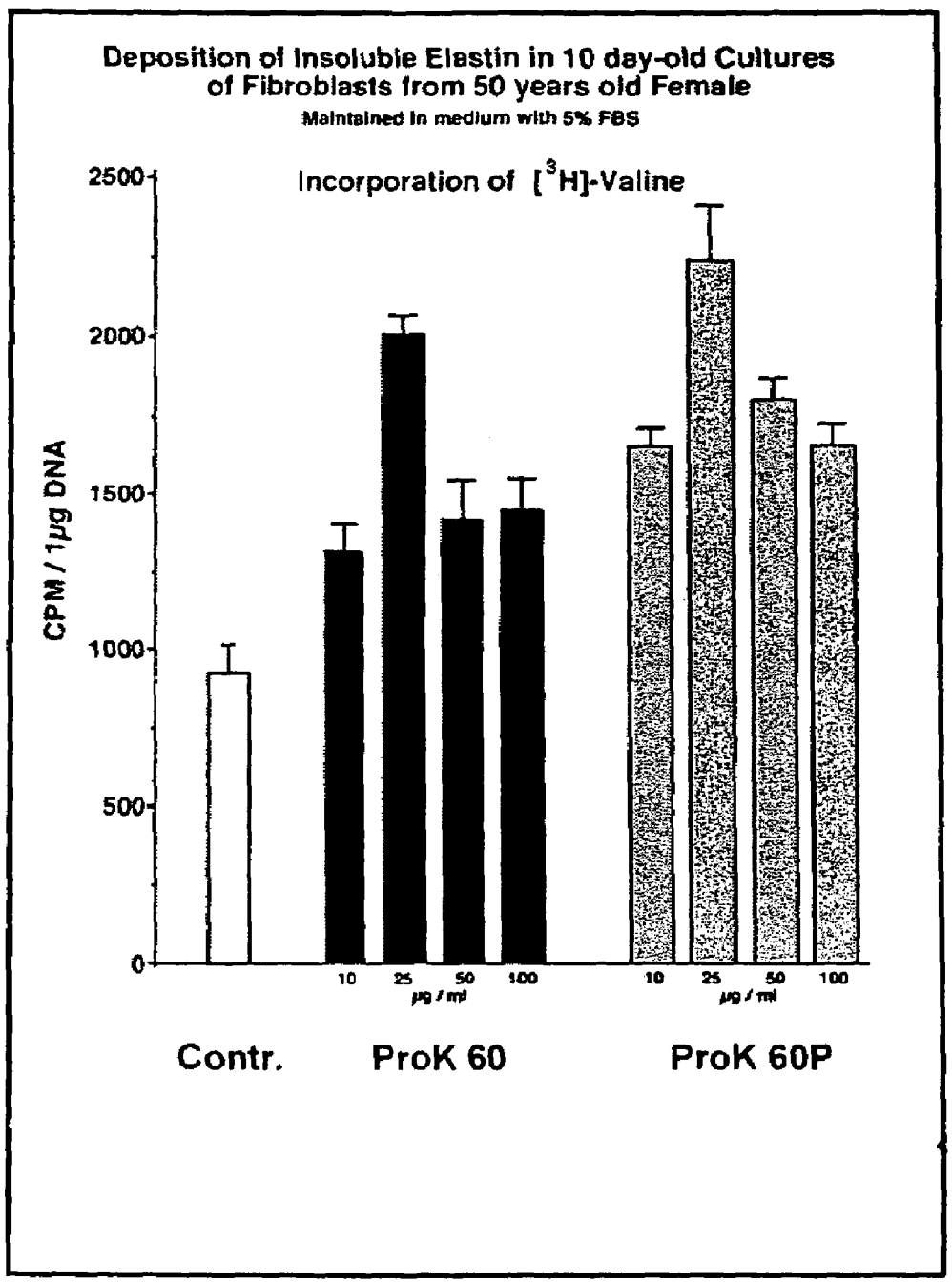
FIG. 5 is an assessment of the deposition of insoluble elastin in fibroblasts.

Refer to FIG. 5, which illustrates the deposition of insoluble elastin in fibroblasts. Given that ProK 40 and ProK 50 preparations inhibited growth of all three fibroblast lines (data not shown), only ProK 60 was subjected to further experimentation. Biochemical assay of newly produced insoluble elastin (metabolically labeled with radioactive valine) indicated that cultures of human skin fibroblasts doubled their deposition of elastin when cultured in the presence of 25 µg/ml of ProK 60 or ProK 60P. Both ProK 60 and ProK 60P across all tested concentration were effective in stimulating elastin deposition.

Figure 6:
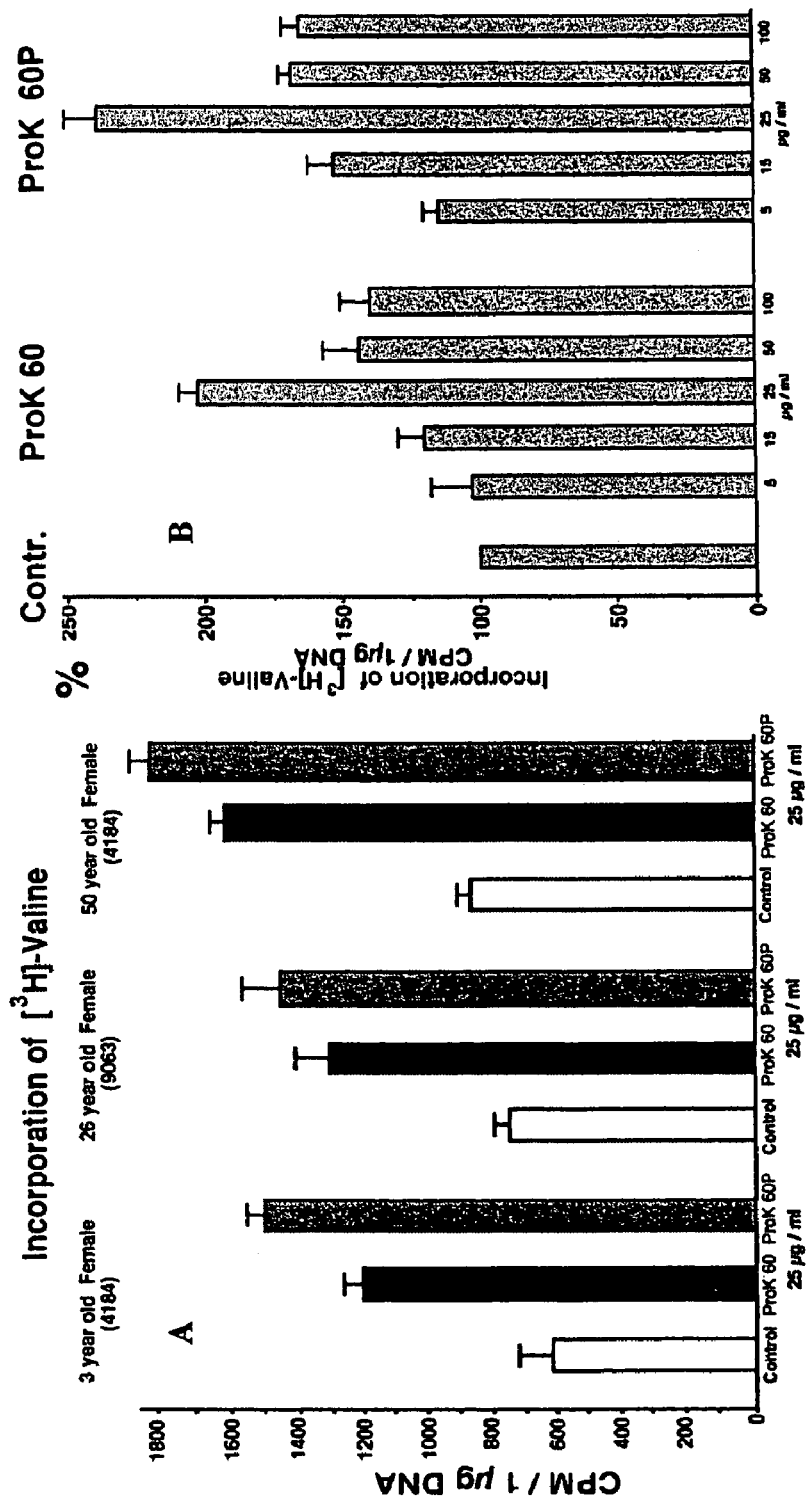
FIG. 6 is an assessment of the deposition of insoluble elastin in fibroblasts.
Figure 7:
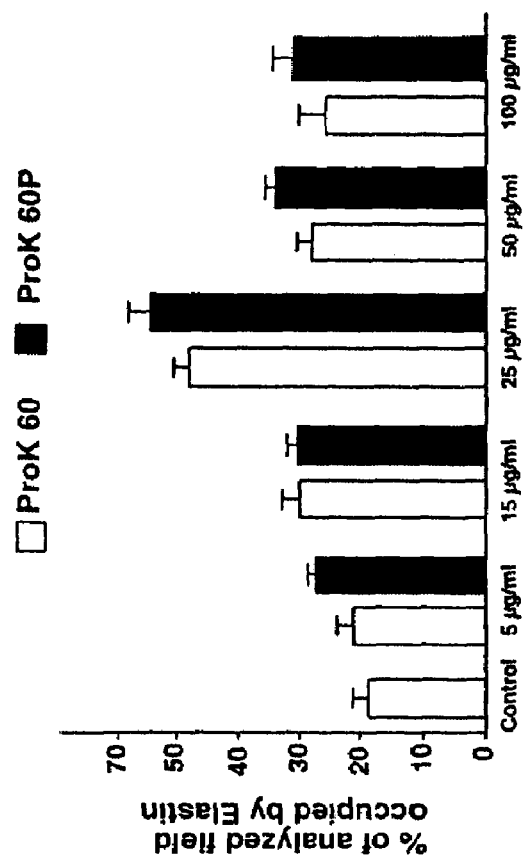
FIG. 7 is an morphometric analysis of elastic fibers in skin fibroblasts.

ProK 60 is the "pure" elastin digest (containing Tris-HCL and Ca-Acetate) and ProK 60P is the preserved version containing cetylpyridinium chloride salts and other chemical preservatives. Results of this assay reading deposition of [$^3$H]-valine-labeled elastin expressed as CPM/1 µg DNA indicated that the increased depositon of elastin (per cell) in cultures of fibroblasts, derived from subjects of different ages, stimulated by ProK 60 and ProK 60P was independent of mitogenic effect in these preparations. The jointly evaluated results of numerous experiments involving cells from all three individuals of different age further confirmed that both preparations stimulate elastogensis in a very broad range of their concentrations, with 25 µg/ml being an effective concentration of these compounds elevating elastogenesis to the levels of about 110-150% of normal values. FIG. 6 illustrates the deposition of insoluble elastin in fibroblasts by incorporation of [$^3$H]-valine, across the three cell lines. Both ProK 60 and ProK 60P elastin digests stimnulate elastin synthesis. FIG. 6 also shows the ProK 60 and ProK 60P tested across various concentrations and across the three cell lines induce elastogenesis. The stimulatory effect of ProK 60 and ProK 60P preparations in concentrations ranging from 5-100 µg/ml was also confirmed by the morphometric analysis of newly synthesized elastic fiber. Refer to FIG. 7.

Figure 8:
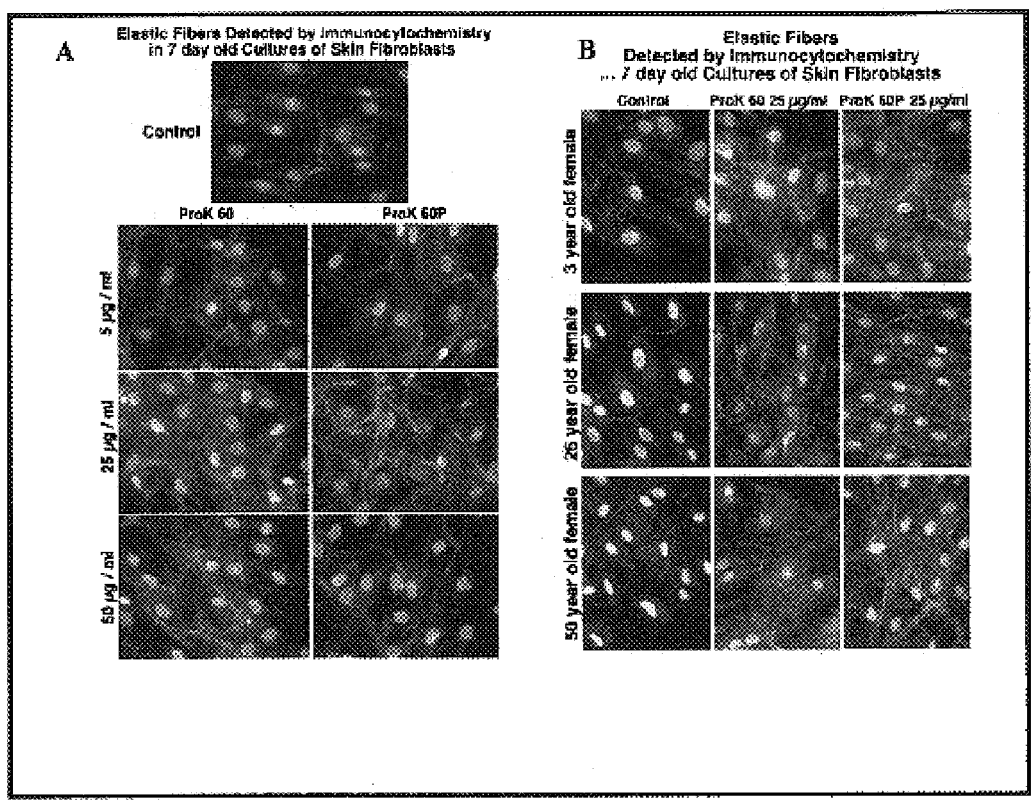
FIG. 8 is an assessment of the deposition of elastic fibers detected by immunocytochemistry in fibroblasts.

FIG. 7 illustrates the morphometric analysis of elastic fibers detected by immunocytochemistry. FIG. 8 illsutrates the immunostraining analysis for ProK 60 and ProK 60P across concentrations and across cell lines. Both formulations induce elastogenesis as seen by the elastic fiber immunocomparison to the control.

Figure 9:
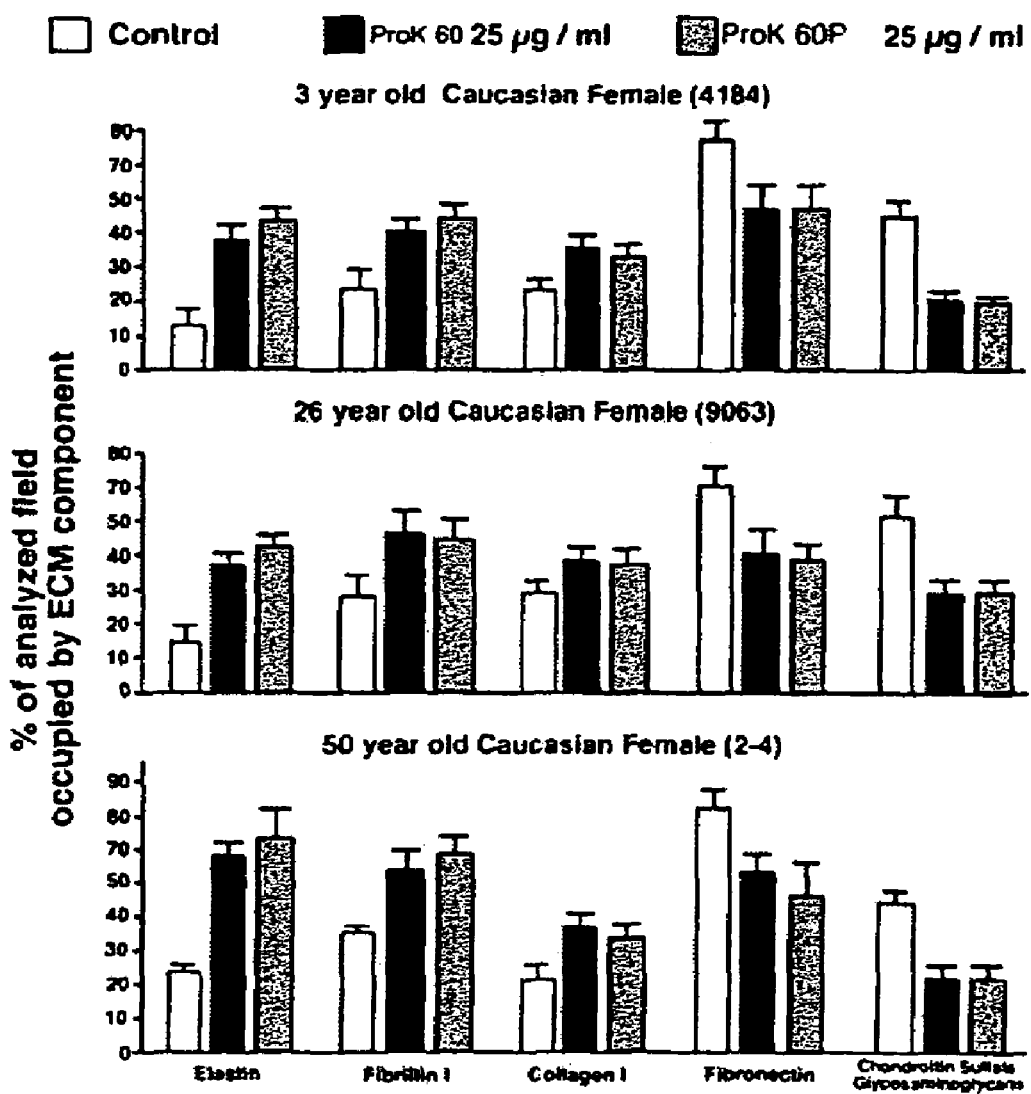
FIG. 9 is an morphometric analysis of extracellular components.
Figure 10:
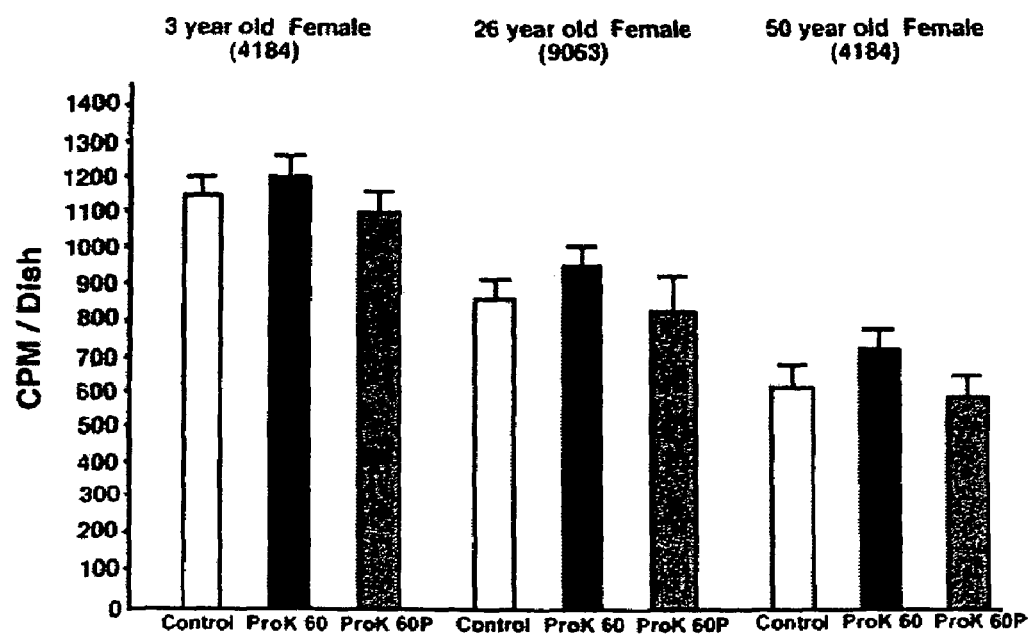
FIG. 10 is an assessment by incorporation of $[^3H]$-thymidine of the cell proliferation of fibroblasts.

Immunocytochemistry and morphometric analysis of cultured human fibroblasts indicated that ProK 60 and ProK 60P stimulated production of fibrillin 1, a major component of microfibrillar scaffold of elastic fibers and lysyl oxidase, enzyme responsible for elastin crosslinking. Refer to FIG. 9. FIG. 9 shows that ProK 60 and ProK 60P compositions affected the synthesis of other extracellular proteins, across the cell lines, over a range of concentrations. Specifically, fibrillin 1 and lysyl oxidase were stimulated in the fibroblasts. Morphometric analysis of cultures immunostained with antibodies recognizing other components of elastic fibers of extracellular matrix demonstrated that both ProK 60 and ProK 60P also stimualted deposition of collagen type I. Refer to FIG. 9. In contrast, Pro K 60 and ProK 60P significantly inhibited production of chondroitin sulfate-containing glycosaminoglycans. Refer to FIG. 9. FIG. 10 illustrates the proliferation of skin fibroblasts assessed by incorporation of [$^3$H]-thymidine across the cell lines.

Figure 11:
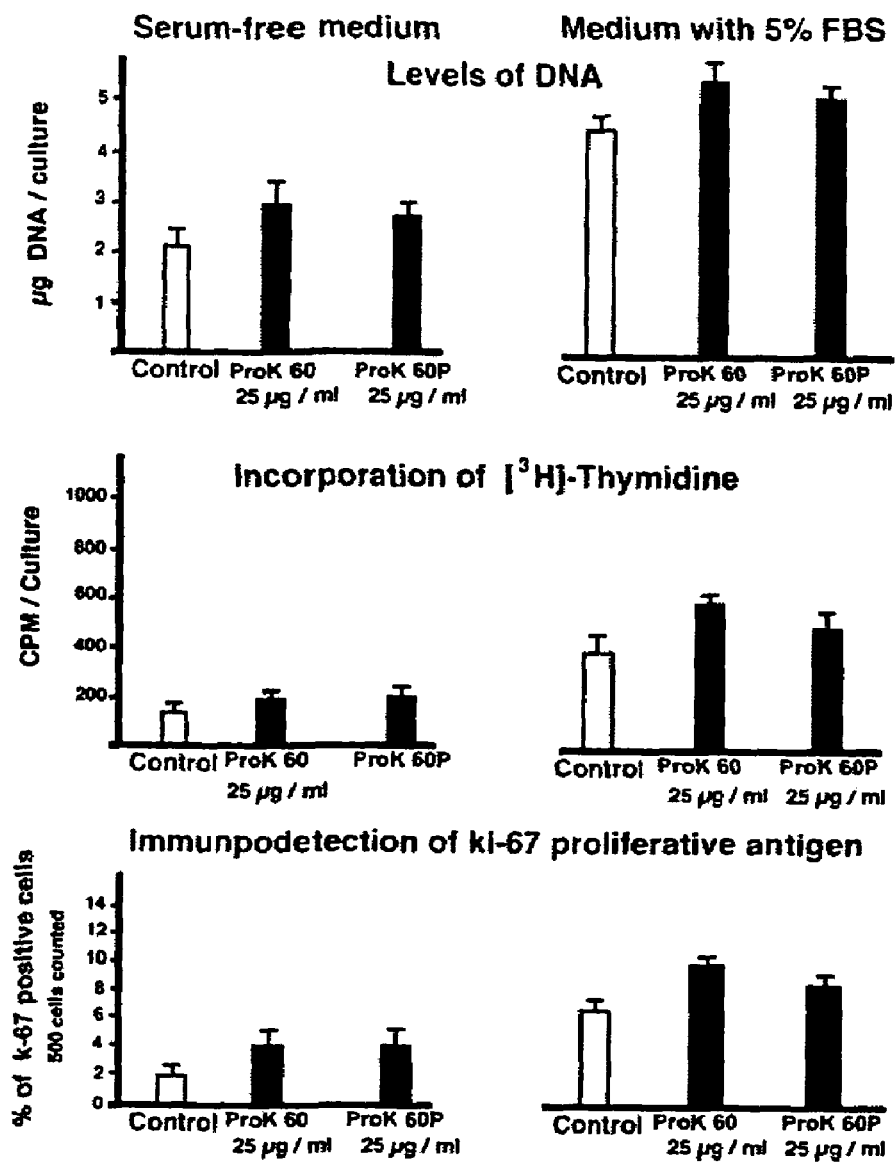
FIG. 11 is an assessment of the proliferation of fibroblasts by DNA content, $[^3H]$-thymidine incorporation and immunodetection of proliferative antigen.

Cell proliferation assessed by incorporation of [$^3$H]-thymidine to fibroblasts derived from all three female subejcts of different ages has indicated that ProK 60 preparation and preferably the 25 μg/ml concentration has a mitogenic activity and stimulated cellular proliferation of treated fibroblast by an average of 10-15% over the control. The proliferative effect of ProK 60 was also confirmed by an assay of total DNA assay and by immunochemical detection of proliferative antigen Ki67. Refer to FIG. 11. FIG. 11 illustrates the proliferation of fibroblasts derived from the 50 year old subject as assessed by DNA content, [$^3$H]-thymidine incorporation and immunodetection of Ki-67 proliferative antigen. Both ProK 60 and ProK 60P in 25 mg/ml concentration were tested.

Although the present invention has been desribed in considerable detail with reference to certain preferred embodiments thereof, other versions are possible. Therefore the spirit and scope of the appended claims should not be limited to the description and the preferred embodiments disclosed herein.

What is claimed is:

1. A composition comprising an excipient and a peptide consisting of the sequence selected from PGGVLPG (SEQ ID NO: 47), VGVVPG (SEQ ID NO: 48), and IGLGPGGV (SEQ ID NO: 49).

2. The composition of claim 1, wherein the composition is in the form selected from the group consisting of an emulsion, lotion, spray, aerosol, powder, ointment, cream, foam, and gel.

3. The composition of claim 1, further including chemical preservatives.

4. The composition of claim 3, wherein the chemical preservative is cetylpyridinium chloride.

5. The composition of claim 1, further comprising an elastin digest derived from proteolytic digestion of Elastin derived from a mammal.

6. The composition of claim 5, wherein the elastin digest comprises a mixture of elastin peptides.

7. The composition of claim 5, wherein the composition is a treatment for the restoration of cutaneous connective tissue.

8. The composition of claim 5, wherein the composition induces cellular proliferation in the tissue to which it is applied.

9. A method of treating an Elastin containing tissue, the method comprising:
   administering to a site in need thereof on a mammal an effective amount of the composition of claim 1, for improving the appearance or elasticity of said tissue.

10. The method of claim 9, further including heating said site.

11. The method of claim 9, wherein administration establishes an effective concentration of said composition at said site.

12. The method of claim 9, wherein administration is by injection or topical administration.

13. The method of claim 9, wherein the composition stimulates the production of fibrillin in the tissue to which it is administered.

14. The method of claim 9, wherein the composition stimulates the endogenous synthesis and deposition of Elastin in the tissue to which it is administered.

15. The method of claim 9, wherein the composition stimulates cell proliferation in the tissue to which it is administered.

16. The method of claim 9, wherein the composition stimulates the deposition of collagen in the tissue to which it is administered.

17. The method of claim 9, wherein the composition stimulates the production of lysyl oxidase in the tissue to which it is administered.

18. The method of claim 9, wherein the composition stimulates cell migration to age-depleted zones of the skin.

19. The method of claim 9, wherein the composition inhibits production of chondroitin sulfate-containing glycosaminoglycans.

20. The method of claim 9, wherein the composition improves the appearance of a site presenting visible lines or wrinkles.

21. The method of claim 9, wherein the composition improves the appearance of a site comprising scar tissue.

22. The method of claim 9, wherein the tissue comprises mouth tissue.

23. The method of claim 9, wherein the tissue comprises follicles.

24. The method of claim 9, wherein the tissue comprises corneal tissue.

25. The method of claim 9, wherein the composition further comprises a mixture of elastin peptides.

26. The method of claim 9, wherein the composition further comprises epitopes, cytokines, growth factors and di-peptides.

27. A composition comprising an elastin digest derived from proteolytic digestion of Elastin derived from a mammal and a peptide selected from the group consisting of PGGVLPG (SEQ ID NO: 47), VGVVPG (SEQ ID NO: 48), and IGLGPGGV (SEQ ID NO: 49).

28. The composition of claim 27, wherein the elastin digest comprises a mixture of elastin peptides.

29. The composition of claim 27, wherein the composition is a treatment for the restoration of cutaneous connective tissue.

30. The composition of clain 27, wherein the composition induces cellular proliferation in the tissue to which it is applied.

31. A peptide consisting of the sequence PGGVLPG (SEQ ID NO. 47).

32. A peptide consisting of the sequence VGVVPG (SEQ ID NO. 48).

33. A peptide consisting of the sequence IGLGPGGV (SEQ ID NO. 49).

* * * * *